United States Patent
Lindsey et al.

(10) Patent No.: US 9,303,165 B2
(45) Date of Patent: Apr. 5, 2016

(54) BACTERIOCHLORIN IMIDES

(75) Inventors: Jonathan S. Lindsey, Raleigh, NC (US); Michael Krayer, Raleigh, NC (US)

(73) Assignee: North Carolina State University, Raleigh, NC (US)

(*) Notice: Subject to any disclaimer, the term of this patent is extended or adjusted under 35 U.S.C. 154(b) by 0 days.

(21) Appl. No.: 14/117,212

(22) PCT Filed: May 30, 2012

(86) PCT No.: PCT/US2012/039987
§ 371 (c)(1),
(2), (4) Date: Nov. 12, 2013

(87) PCT Pub. No.: WO2012/166792
PCT Pub. Date: Dec. 6, 2012

(65) Prior Publication Data
US 2014/0154186 A1    Jun. 5, 2014

Related U.S. Application Data

(60) Provisional application No. 61/491,601, filed on May 31, 2011.

(51) Int. Cl.
| | |
|---|---|
| A61K 41/00 | (2006.01) |
| A61K 49/00 | (2006.01) |
| C09B 47/00 | (2006.01) |
| C07D 487/22 | (2006.01) |
| G01N 33/58 | (2006.01) |

(52) U.S. Cl.
CPC ........... C09B 47/00 (2013.01); A61K 41/0071 (2013.01); A61K 49/0036 (2013.01); C07D 487/22 (2013.01); G01N 33/582 (2013.01)

(58) Field of Classification Search
CPC ........ A61K 31/40; A61K 41/00; A61K 49/00
See application file for complete search history.

(56) References Cited

U.S. PATENT DOCUMENTS

| | | | |
|---|---|---|---|
| 7,534,807 B2 * | 5/2009 | Kim et al. | 514/410 |
| 2004/0044197 A1 | 3/2004 | Pandey et al. | |
| 2009/0226467 A1 | 9/2009 | Kim et al. | |

FOREIGN PATENT DOCUMENTS

| | | |
|---|---|---|
| WO | WO 2004/002476 A2 | 1/2004 |
| WO | WO 2004/110255 A2 | 12/2004 |
| WO | WO 2008/023378 A1 | 2/2008 |

OTHER PUBLICATIONS

Michael Krayer et al. De novo synthesis and photophysical characterization of annulated bacteriochlorins. Mimicking and extending the properties of bacteriochlorophylls, New. J. Chem, 2011, 35, 587-601.*

Ptaszek M et al. De novo synthesis of long-wavelength absorbing chlorin-13,15-dicarboximides. Journal of Organic Chemistry. 2010; 75(5): 1659-1673.

International Search Report and Written Opinion, PCT/12/39987, mailed Aug. 16, 2012.

Krayer M et al. De novo synthesis and photophysical characterization of annulated bacteriochlorins. Mimicking and extending the properties of bateriochlorophylls. New J. Chem. 2011; 35: 587-601.

European Search Report and Opinion, EP 12792708.5, mailed Oct. 2, 2014.

* cited by examiner

*Primary Examiner* — Michael G Hartley
*Assistant Examiner* — Jagadishwar Samala
(74) *Attorney, Agent, or Firm* — Myers Bigel & Sibley, P.A.

(57) ABSTRACT

Compound of Formula I: are described, along with compositions containing the same and methods of use thereof.

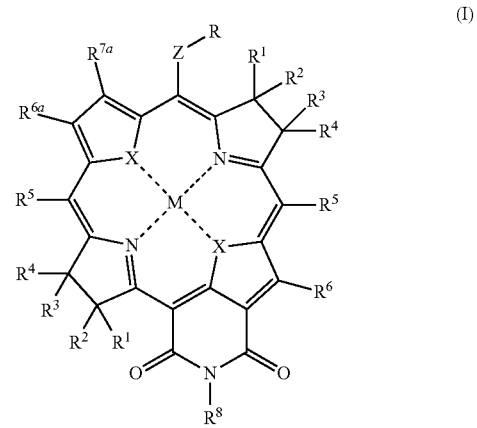

16 Claims, 2 Drawing Sheets

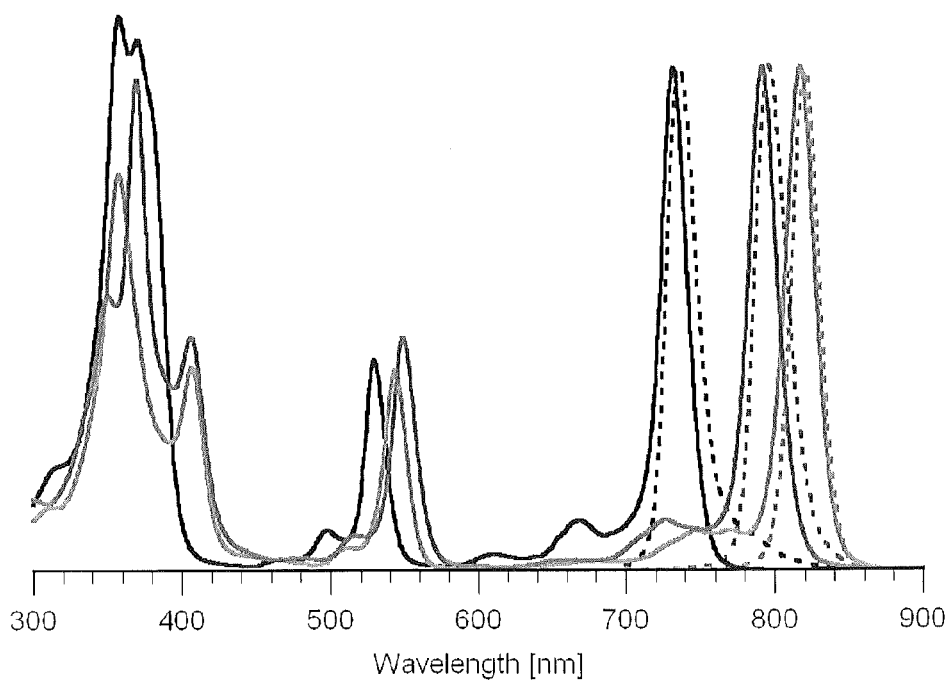
Figure 1. Absorption (—— solid lines) and emission (--- dashed lines) spectra (normalized) in toluene at room temperature of MeOBOP (blue/B), MeOBC-I (green/G), and HBC-I (magenta/M).

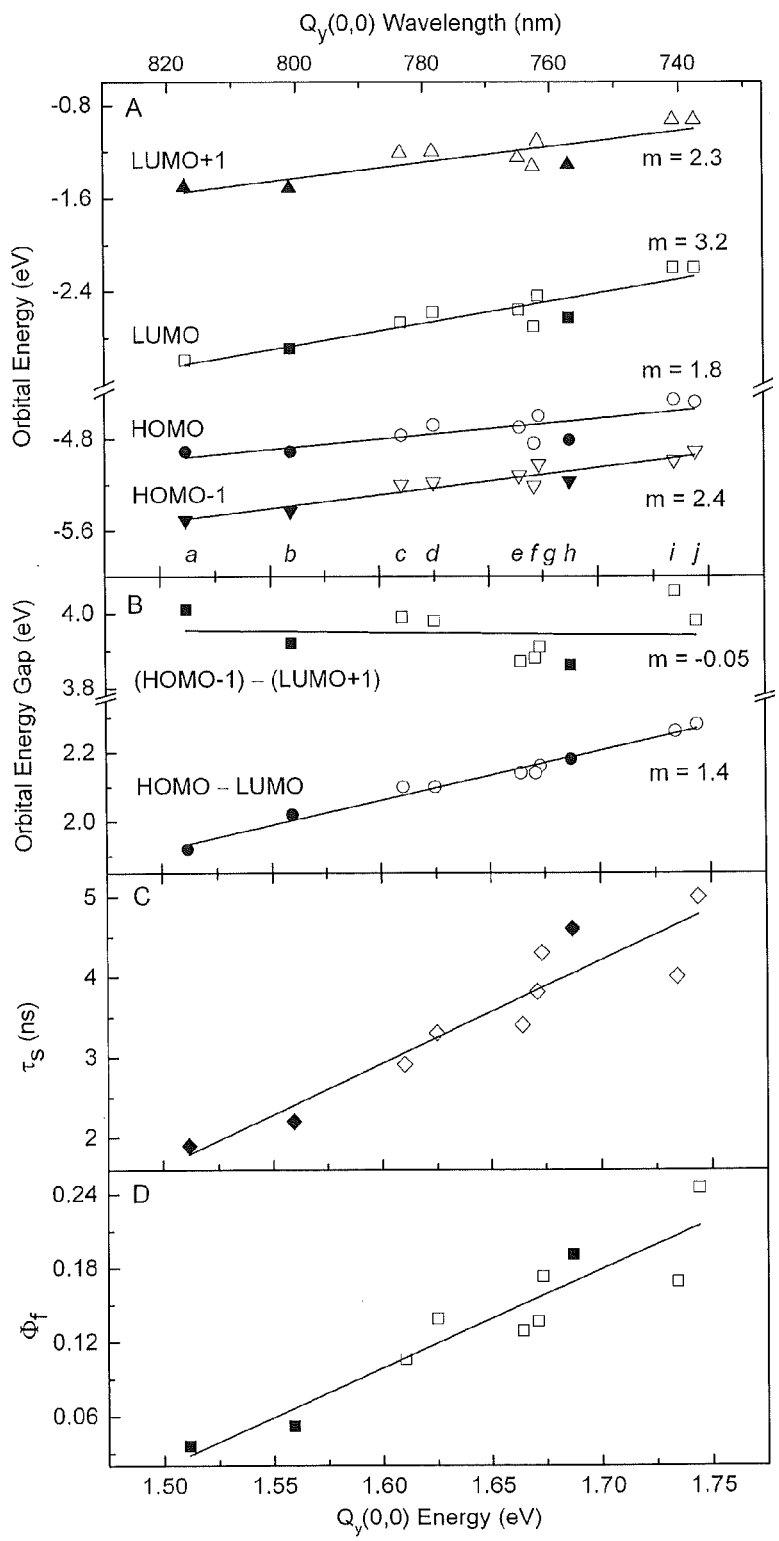
Figure 2. Orbital energies, energy gaps, singlet excited-state lifetime, and fluorescence yield as a function of the $Q_y(0,0)$ energy (bottom axis) and wavelength (top axis).

BACTERIOCHLORIN IMIDES

RELATED APPLICATIONS

This application is a 35 U.S.C. §371 national phase entry of PCT Application PCT/2012/039987, filed May 30, 2012, and published in English on Dec. 6, 2012, as International Publication No. WO 2012/166792 A1, and which claims the benefit under 35 U.S.C. §119(e) of U.S. Provisional Patent Application Ser. No. 61/491,601, filed May 31, 2011, the disclosure of each of which is incorporated herein by reference in its entirety.

STATEMENT OF FEDERAL SUPPORT

This invention was made with US Government support under Grant Number DE-FG02-96ER14632 from the US Department of Energy. The US Government has certain rights to this invention.

FIELD OF THE INVENTION

The present invention concerns bacteriochlorin imide compounds, compositions containing the same, and methods of making and using the same.

BACKGROUND OF THE INVENTION

Bacteriochlorins absorb strongly in the near-infrared spectral region[1] and hence are attractive candidates for a wide variety of photochemical studies, including artificial photosynthesis,[2-9] photodynamic therapy (PDT),[10-23] optical imaging,[24-26] and perhaps flow cytometry.[24,27] Naturally occurring bacteriochlorophylls a, b, and g contain the bacteriochlorin chromophore and provide the basis for light-harvesting processes and electron-transfer reactions in bacterial photosynthesis (Chart 1, panel A).[28] Bacteriochlorophylls also possess a five-membered ring (ring E) that encompasses the 13- and 15-positions; the ring contains a $13^1$-oxo moiety and a $13^2$-methoxycarbonyl substituent. Synthetic manipulation of bacteriochlorophylls has afforded a number of derivatives including (i) bacteriopyropheophorbides, which lack the $13^2$-methoxycarbonyl substituent, the phytyl-like chain, and the central magnesium;[2-4,29,30] and (ii) bacteriopurpurinimides (hereafter referred to as bacteriochlorin-imides), which bear a six-membered imide ring (Chart 1, panel B).[6,12,16,17,31-37]

The presence of the imide ring in bacteriochlorin-imides provides a number of attractions including (1) a hyperchromic and bathochromic shift of the long-wavelength absorption band; (2) the ability to introduce diverse groups at the nitrogen of the imide ring;[38] and (3) increased stability of the macrocycle toward routine handling due to the presence of the second carbonyl group at the 15-position. So far, bacteriochlorins bearing the five membered oxopentano or six-membered imide ring have only been available from the natural compounds or upon semisynthesis therefrom, respectively, although synthetic porphyrins and chlorins with a wide variety of annulated rings have been prepared.[39,40] Two significant problems in the preparation of derivatives of bacteriochlorophylls include limited stability[36,41,42] and poor synthetic malleability owing to the presence of a nearly full complement of substituents about the perimeter of the macrocycle.[13,18] The synthesis of bacteriochlorins by reduction or addition of porphyrins or chlorins is appropriate for a number of applications but generally suffers from a lack of regiocontrol.[43]

Chart 1.
(A) Naturally occurring bacteriochlorophylls. (B) Derivatives of naturally occurring bacteriochlorophylls. (C) Nomenclature of the core macrocycles.

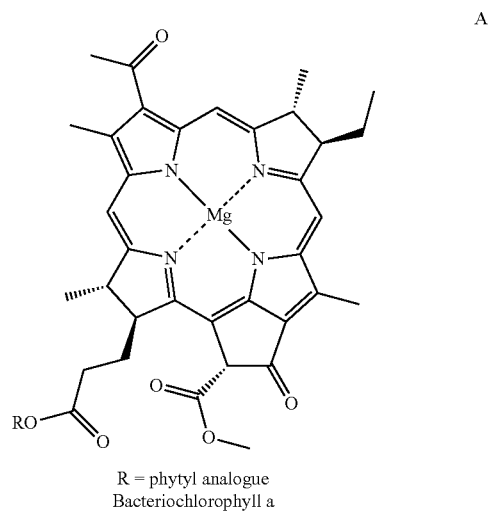

R = phytyl analogue
Bacteriochlorophyll a

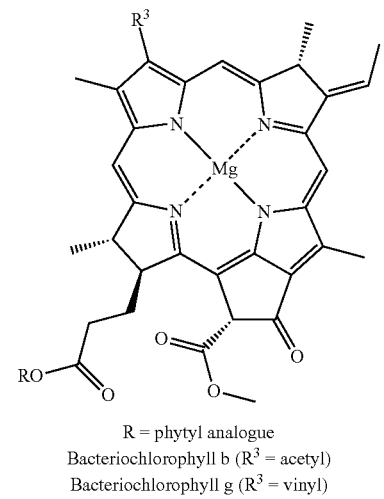

R = phytyl analogue
Bacteriochlorophyll b ($R^3$ = acetyl)
Bacteriochlorophyll g ($R^3$ = vinyl)

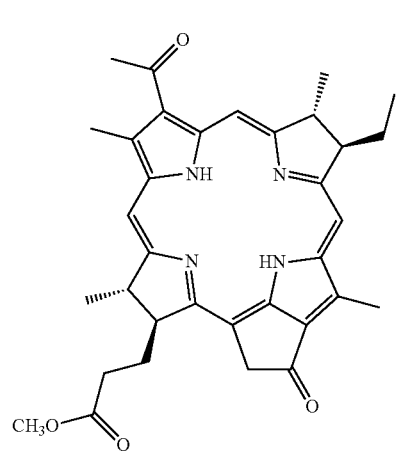

Methyl bacteriopyropheophorbide a

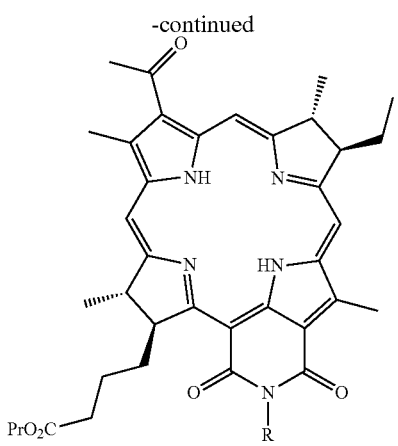

R = alkyl, amino, methoxy or hydroxy
Bacteriopurpurinimides

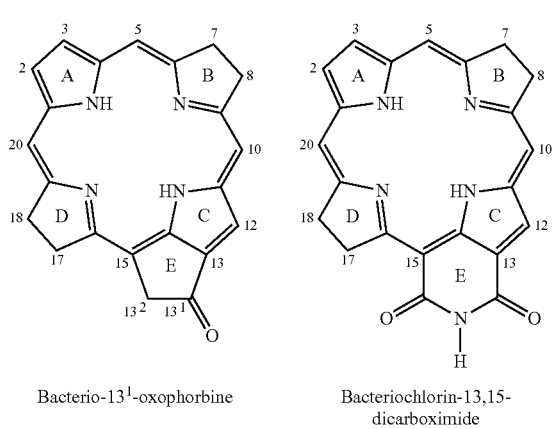

Bacterio-13¹-oxophorbine    Bacteriochlorin-13,15-dicarboximide

Over the past decade we have been developing a de novo synthesis of bacteriochlorins.[44-46] The route affords bacteriochlorins wherein each pyrroline ring contains a geminal dimethyl group rather than the trans-dialkyl and exo-ethylidene moieties of the naturally occurring bacteriochlorophylls. The geminal dimethyl group has the attractive feature of stabilizing the macrocycle toward adventitious dehydrogenation. Synthetic bacteriochlorins bearing diverse substituents at specific sites in the pyrrolic units have been prepared, and selected derivatization processes of the bacteriochlorins have been examined (including regioselective bromination); however, no annulated rings have yet been introduced.[44-51]

SUMMARY OF THE INVENTION

A first aspect of the invention is a compound of Formula I:

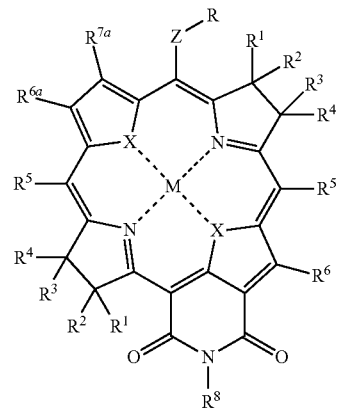

(I)

wherein:

M is a metal or is absent;

X is selected from the group consisting of Se, NH, $CH_2$, O and S;

Z is O, S or a covalent bond;

R and each $R^1$ and $R^2$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; or $R^1$ and $R^2$ together are =O or spiroalkyl;

each $R^3$ and $R^4$ is independently selected from the group consisting of alkyl, cycloalkyl, aryl, and arylalkyl;

each $R^5$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; and $R^6$, $R^{6a}$ and $R^{7a}$ are each independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; and $R^8$ is selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups.

In some embodiments, the targeting group is selected from the group consisting of proteins, peptides, and nucleic acids.

A further aspect of the invention is a method of detecting cells or particles by flow cytometry, wherein said cells or particles are labelled with a detectable luminescent compound, the improvement comprising utilizing a bacteriochlorin as the luminescent compound, wherein said bacteriochlorin is a bacteriochlorin-imide compound as described herein.

A further aspect of the invention is a composition consisting of a bacteriochlorin-imide compound as described herein, optionally in a solvent, wherein:

said composition has a peak molar absorption coefficient in solution of 10,000 to 300,000 $M^{-1}cm^{-1}$ at a wavelength between 700 and 1000 nanometers; and/or said composition has a loss of not more than 20 percent of said compound when stored in a sealed vessel at room temperature in the absence of ambient light for at least 3 months.

A further aspect of the invention is a pharmaceutical composition comprising a bacteriochlorin-imide compound as described herein in a pharmaceutically acceptable carrier.

A further aspect of the invention is a method for treating a target in a subject in need thereof, comprising: (i) administering to said subject the bacteriochlorin imide compound as described herein or a pharmaceutically acceptable conjugate thereof that preferentially associates with the target, and (ii) irradiating the target with light of a wavelength and intensity sufficient to treat said target (e.g., wherein the target is selected from the group consisting of: a vascular endothelial tissue, a neovasculature tissue, a neovasculature tissue present in an eye, an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumors of a lung, a nonsolid tumor, malignant cells of one of a hematopoietic tissue and a lymphoid tissue, lesions in a vascular system, a diseased bone marrow, and diseased cells in which the disease is one of an autoimmune and an inflammatory disease; or wherein the target composition is selected from the group consisting of bacteria, viruses, fungi, protozoa, and toxins).

A further aspect of the invention is a photodynamic therapy method for treating hyperproliferative tissue in a subject in need thereof, comprising: (i) administering to said subject a bacteriochlorin-imide compound as described herein or a pharmaceutically acceptable conjugate thereof that preferentially associates with the hyperproliferative tissue, and (ii) irradiating the target with light of a wavelength and intensity sufficient to activate the compound, and thereby treat said hyperproliferative tissue.

A further aspect of the invention is a method for detecting the presence of a hyperproliferative tissue in a subject, comprising: (i) administering to the subject a bacteriochlorin-imide compound as described herein or a pharmaceutically acceptable conjugate thereof that preferentially associates with the hyperproliferative tissue; and then (ii) visualizing the compound within the patient.

A further aspect of the invention is a kit to treat hyperproliferative disorders, comprising the bacteriochlorin-imide compound as described herein or a pharmaceutically acceptable conjugate thereof and instructions teaching a method of photodynamic therapy.

A further aspect of the invention is, in a light harvesting rod, the improvement comprising utilizing a bacteriochlorin-imide compound as described herein as at least one chromophore therein.

A further aspect of the invention is, in a solar cell, the improvement comprising utilizing a bacterichlorin-imide compound as described herein as the chromophore or photosensitizer therein; wherein said bacteriochlorin-imide compound of is in monomeric form or is optionally linked to at least one additional chromophore to form a light harvesting rod (e.g., wherein said solar cell is a high surface area colloidal semiconductor film solar cell (Gratzel cell)).

A further aspect of the invention is, in an information storage device utilizing a charge storage molecule in monomeric or polymeric form, the improvement comprising utilizing as said charge storage molecule a bacteriochlorin-imide compound as described herein.

The foregoing and other objects and aspects of the invention are explained in greater detail in the drawings herein and the specification set forth below.

BRIEF DESCRIPTION OF THE DRAWINGS

FIG. 1. Absorption (— solid lines) and emission (--- dashed lines) spectra (normalized) in toluene at room temperature of MeOBOP (blue), MeOBC-I (green), and HBC-I (magenta).

FIG. 2. Orbital energies, energy gaps, singlet excited-state lifetime, and fluorescence yield as a function of the $Q_y(0,0)$ energy (bottom axis) and wavelength (top axis). For each plot, the solid symbols are for the three target compounds, MeOBOP, MeOBC-I and HBC-I, and the open symbols are for the benchmark bacteriochlorins. The letter code (a-j) at the bottom of panel A gives the left-to-right order of the data points for each plot in the figure and identifies the compounds as listed in the first two columns of Table 1.

DETAILED DESCRIPTION OF THE PREFERRED EMBODIMENTS

"Acetal" as used herein refers to a group of the formula:

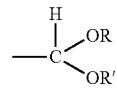

where R and R' are each suitable groups, e.g., groups independently selected from the group consisting of alkyl, aryl, alkylaryl, or where R and R' together form a group —R"— where R" is an alkylene (i.e., cycloalkyl). The acetal is preferably reasonably robust, and hence it is preferred that at least one, or more preferably both, of R and R' is not methyl, and it is particularly preferred that neither R nor R' is H.

"Aldehyde" as used herein refers to a group of the formula:

"Halo" as used herein refers to any suitable halogen, including. —F, —Cl, —Br, and —I.

"Mercapto" as used herein refers to an —SH group.

"Azido" as used herein refers to an —N$_3$ group.

"Cyano" as used herein refers to a —CN group.

"Hydroxyl" as used herein refers to an —OH group.

"Nitro" as used herein refers to an —NO$_2$ group.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with 1, 2, 3 or more groups independently selected from alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted 1, 2, 3 or more times with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted 1, 2, 3 or more times with the same groups as set forth in connection with alkyl and loweralkyl above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted 1, 2, 3 or more times with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —NH$_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —NR$_a$R$_b$, where R$_a$ and R$_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —NR$_a$R$_b$, where R$_a$ is an acyl group as defined herein and R$_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Amide" as used herein alone or as part of another group refers to a —C(O)NR$_a$R$_b$ radical, where R$_a$ and R$_b$ are any suitable substituent such as alkyl, cycloalkyl, alkenyl, alkynyl or aryl.

"Sulfonamide" as used herein alone or as part of another group refers to a —S(O)$_2$NR$_a$R$_b$ radical, where R$_a$ and R$_b$ are any suitable substituent such as H, alkyl, cycloalkyl, alkenyl, alkynyl or aryl.

"Urea" as used herein alone or as part of another group refers to an —N(R$_c$)C(O)NR$_a$R$_b$ radical, where R$_a$, R$_b$ and R$_c$ are any suitable substituent such as H, alkyl, cycloalkyl, alkenyl, alkynyl or aryl.

"Alkoxyacylamino" as used herein alone or as part of another group refers to an —N(R$_a$)C(O)OR$_b$ radical, where R$_a$, R$_b$ are any suitable substituent such as H, alkyl, cycloalkyl, alkenyl, alkynyl or aryl.

"Aminoacyloxy" as used herein alone or as part of another group refers to an —OC(O)NR$_a$R$_b$ radical, where R$_a$ and R$_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is intended to include both substituted and unsubstituted cycloalkyl unless otherwise indicated and these groups may be substituted 1, 2, 3 or more times with the same groups as set forth in connection with alkyl and loweralkyl above. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. The term "heterocyclo" or "heterocyclic group" is intended to include both substituted and unsubstituted heterocyclo unless otherwise indicated and these groups may be substituted 1, 2, 3 or more times with the same groups as set forth in connection with alkyl and loweralkyl above. Preferred heterocyclo groups include pyridyl and imidazolyl groups, these terms including the quaternized derivatives thereof, including but not limited to quaternary pyridyl and imidazolyl groups, examples of which include but are not limited to:

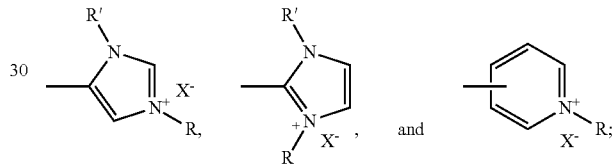

where R and R' are each a suitable substitutent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X$^-$ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted 1, 2, 3 or more times with the same groups as set forth in connection with alkyl and loweralkyl above.

"Treatment" as used herein means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated. As used herein, amelioration of the symptoms of a particular disorder by administration of a particular compound or pharmaceutical composition refers to any lessening, whether permanent or temporary, lasting or transient that can be attributed to or associated with administration of the composition.

"Prodrug" as used herein is a compound that, upon in vivo administration, is metabolized by one or more steps or processes or otherwise converted to the biologically, pharmaceutically or therapeutically active form of the compound.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Infecting agent" as used herein denotes invading microbes or parasites. As used herein, "microbe" denotes virus, bacteria, rickettsia, mycoplasma, protozoa, fungi and like microorganisms, and "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like.

"Tumor" as used herein denotes a neoplasm, and includes both benign and malignant tumors. This term particularly includes malignant tumors which can be either solid (such as a breast, liver, or prostate carcinoma) or non-solid (such as a leukemia). Tumors can also be further divided into subtypes, such as adenocarcinomas (e.g. of the breast, prostate or lung).

"Target" as used herein denotes the object that is intended to be detected, diagnosed, impaired or destroyed by the methods provided herein, and includes target cells, target tissues, and target compositions. "Target tissues" and "target cells" as used herein are those tissues that are intended to be impaired or destroyed by this treatment method. Photosensitizing compounds bind to or collect in these target tissues or target cells; then when sufficient radiation is applied, these tissues or cells are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included among target cells are cells undergoing substantially more rapid division as compared to non-target cells.

"Non-target tissues" as used herein are all the tissues of the subject which are not intended to be impaired or destroyed by the treatment method. These non-target tissues include but are not limited to healthy blood cells, and other normal tissue, not otherwise identified to be targeted.

"Target compositions" as used herein are those compositions that are intended to be impaired or destroyed by this treatment method, and may include one or more pathogenic agents, including but not limited to bacteria, viruses, fungi, protozoa, and toxins as well as cells and tissues infected or infiltrated therewith. The term "target compositions" also includes, but is not limited to, infectious organic particles such as prions, toxins, peptides, polymers, and other compounds that may be selectively and specifically identified as an organic target that is intended to be impaired or destroyed by this treatment method.

"Hyperproliferative tissue" as used herein means tissue that grows out of control and includes neoplastic tissue, tumors and unbridled vessel growth such as blood vessel growth found in age-related macular degeneration and often occurring after glaucoma surgeries.

"Hyperproliferative disorders" as used herein denotes those conditions disorders sharing as an underlying pathology excessive cell proliferation caused by unregulated or abnormal cell growth, and include uncontrolled angiogenesis. Examples of such hyperproliferative disorders include, but are not limited to, cancers or carcinomas, acute and membrano-proliferative glomerulonephritis, myelomas, psoriasis, atherosclerosis, psoriatic arthritis, rheumatoid arthritis, diabetic retinopathies, macular degeneration, corneal neovascularization, choroidal hemangioma, recurrence of pterygii, and scarring from excimer laser surgery and glaucoma filtering surgery.

"Therapeutically effective dose" as used herein is a dose sufficient to prevent advancement, or to cause regression of the disease, or which is capable of relieving symptoms caused by the disease.

"Irradiating" and "irradiation" as used herein includes exposing a subject to all wavelengths of light. Preferably, the irradiating wavelength is selected to match the wavelength(s) which excite the photosensitive compound. Preferably, the radiation wavelength matches the excitation wavelength of the photosensitive compound and has low absorption by the non-target tissues of the subject, including blood proteins.

"Biological materials" as used herein refers to both tissues (such as biopsy tissues) and cells, as well as biological fluids such as blood, urine, plasma, cerebrospinal fluid, mucus, sputum, etc.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

While one preferred embodiment of the present invention is drawn to the use of light energy for administering photodynamic therapy (PDT) to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical, and electrical. For example, sonodynamically induced or activated agents include, but are not limited to: gallium-porphyrin complex (see Yumita et al., Cancer Letters 112: 79-86 (1997)), other porphyrin complexes, such as protoporphyrin and hematoporphyrin (see Umemura et al., Ultrasonics Sonochemistry 3: S187-S191 (1996)); other cancer drugs, such as daunorubicin and adriamycin, used in the presence of ultrasound therapy (see Yumita et al., Japan J. Hyperthermic Oncology 3(2):175-182 (1987)).

"Coupling agent" as used herein, refers to a reagent capable of coupling a photosensitizer to a targeting group.

"Targeting group" refers to a compound that homes in on or preferentially associates or binds to a particular tissue, receptor, infecting agent or other area of the body of the subject to be treated, such as a target tissue or target composition. Examples of a targeting group include but are not limited to a ligand, one member of a ligand-receptor binding pair, nucleic acids or polynucleic acids such as DNA (including derivatives thereof) of any suitable length (e.g., 5 or 10 to 50 or 100 nucleotides in length), proteins and peptides (such as antibodies), and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (antiligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-.alpha. and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

Subjects to be treated by the methods of the present invention for diagnostic or therapeutic purposes include both human subjects and animal subjects (particularly mammalian subjects such as dogs, cats, horses, monkeys, chimpanzees, etc.) for veterinary purposes.

The disclosures of all United States Patent references cited herein are to be incorporated by reference herein as if fully set forth.

1. Compounds and Methods of Making.

As noted above, the present invention provides compounds of Formula I:

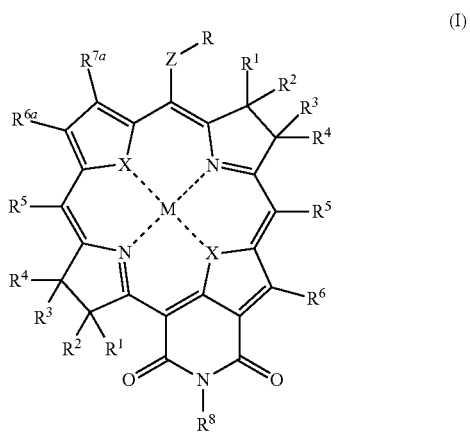

wherein:
M is a metal or is absent;
X is selected from the group consisting of Se, NH, $CH_2$, O and S;
Z is O, S or a covalent bond;
R and each $R^1$ and $R^2$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; or $R^1$ and $R^2$ together are =O or spiroalkyl;

each $R^3$ and $R^4$ is independently selected from the group consisting of alkyl, cycloalkyl, aryl, and arylalkyl;

each $R^5$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, hetero aryl alkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; and $R^6$, $R^{6a}$ and $R^{7a}$ are each independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; and $R^8$ is selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups.

Compounds of Formula I may be made by the reaction of a compound of Formula II:

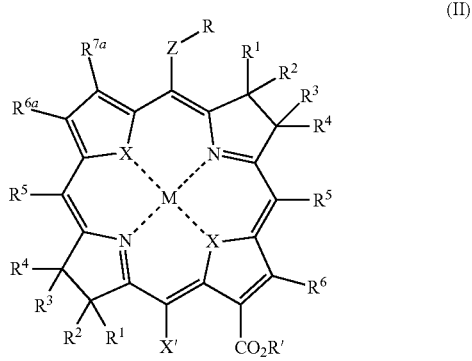

(II)

with a compound of the formula $R^8NH_2$ and carbon monoxide in an organic solvent in the presence of a base and a transition metal catalyst to produce a compound of Formula I, wherein: X' is halo (e.g., Bromo); R' is loweralkyl; and the remaining substituents are as given in connection with Formula I above. $R^8$ can be the same as given in connection with Formula I above, or may be a compound selected to provide a convenient reactive site such as a linking group for further substitution of the product compound. The reactions can be carried out in accordance with known techniques or variations thereof that will be apparent to those skilled in the art. In general, the reactions are carried out in an organic solvent (e.g., toluene, tetrahydrofuran, dimethylformamide) in the presence of a transition metal catalyst such as a palladium catalyst and a base (e.g. cesium carbonate, potassium carbonate, sodium carbonate). Time, temperature and pressure are not critical. However, the pattern of substitutions on the compound of Formula II are important and are discussed in further detail below.

Compounds of Formula I may be metalated with any suitable metal in accordance with known techniques. See, e.g., U.S. Pat. No. 6,208,553. Suitable metals include but are not limited to Pd, Pt, Mg, Zn, Al, Ga, In, Sn, Cu, Ni, and Au. Where the metal is trivalent or tetravalent a counterion is included as necessary in accordance with known techniques.

Linking Groups for Conjugates.

Linking groups are included in compounds of Formula I to provide a reactive site for conjugation so that the compounds may be coupled to or conjugated to other groups such as proteins, peptides, targeting agents such as antibodies, polymers, particles such as nanoparticles, organic, polymeric or inorganic beads, other solid support surfaces, etc., to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R is a reactive group and R' is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidinium, pyridinium). Bioconjugatable groups or linking groups include amines (including amine derivatives) such as isocyanates, isothiocyanates, iodoacetamides, azides, diazonium salts, etc. acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Bioconjugatable groups or linking groups such as the foregoing are known and described in U.S. Pat. Nos. 6,728,129; 6,657,884; 6,212,093; and 6,208,553.

Conjugates.

Other groups can be attached to the bacteriochlorin to form a conjugate by means of a linking group to tune or adjust the solubility properties of the bacteriochlorin, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc. may be attached by means of the linking group. Where such additional compounds are attached to form a conjugate that may be attached directly to the bacteriochlorin or attached by means of an intervening group such as a hydrophilic group, depending upon the particular linking group employed (as noted above).

Hydrophilic Groups.

Compounds of the present invention may include hydrophilic groups coupled at the linking sites noted above, e.g., covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group.

Surface Attachment Groups.

As noted above, compounds of the invention can be substituted with a surface attachment group, which may be in protected or unprotected form. A surface attachment group may be a reactive group coupled directly to the bacteriochlorin, or coupled to the bacteriochlorin by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to alkene, alkyne, alcohol, thiol, selenyl, phosphono, telluryl, cyano, amino, formyl, halo, boryl, and carboxylic acid surface attachment groups such as:

4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl) ethynyl)phenyl; 4-hydroxyphenyl, hydroxymethyl, 2-hydroxyethyl, 3-hydroxypropyl, 2-(4-hydroxyphenyl) ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl) ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl)ethynyl)phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl; 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl,2-tellurylethyl,3-tellurylpropyl, 2-(4-tellurylphenyl)ethynyl, 4-(2-(4-tellurylphenyl)ethynyl) phenyl, 4-tellurylmethylphenyl, 4-(2-tellurylethyl)phenyl, 4-(3-tellurylpropyl)phenyl, 4-(2-(4-tellurylmethylphenyl) ethynyl)phenyl;

4-(dihydroxyphosphoryl)phenyl, (dihydroxyphosphoryl) methyl,2-(dihydroxyphosphoryl)ethyl, 3-(dihydroxyphosphoryl)propyl, 2-[4-(dihydroxyphosphoryl)phenyl] ethynyl, 4-[2-[4-(dihydroxyphosphoryl)phenyl]ethynyl] phenyl, 4-[(dihydroxyphosphoryl)methyl]phenyl, 4-[2-(dihydroxyphosphoryl)ethyl]phenyl, 4-[2-[4-(dihydroxyphosphoryl)methylphenyl]ethynyl]phenyl;

4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-(hydroxy(mercapto)phosphoryl)phenyl]ethynyl, 4-[2-[4-(hydroxy(mercapto)phosphoryl)phenyl]ethynyl] phenyl, 4-[(hydroxy(mercapto)phosphoryl)methyl]phenyl, 4-[2-(hydroxy(mercapto)phosphoryl)ethyl]phenyl, 4-[2-[4-(hydroxy(mercapto)phosphoryl)methylphenyl] ethynyl]phenyl;

4-cyanophenyl, cyanomethyl, 2-cyanoethyl, 3-cyanopropyl, 2-(4-cyanophenyl)ethynyl, 4-[2-(4-cyanophenyl)ethynyl] phenyl, 4-(cyanomethyl)phenyl, 4-(2-cyanoethyl)phenyl, 4-[2-[4-(cyanomethyl)phenyl]ethynyl]phenyl;

4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl;

4-formylphenyl, 4-bromophenyl, 4-iodophenyl, 4-vinylphenyl, 4-ethynylphenyl, 4-allylphenyl, 4-[2-(trimethylsilyl) ethynyl]phenyl, 4-[2-(triisopropylsilyl)ethynyl]phenyl,4-(4,4,5,5-tetramethyl-1,3,2-dioxaborolan-2-yl)phenyl; formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl; 4-(bromomethyl)phenyl, and 2-bromoethyl.

In addition to the monodentate linker-surface attachment groups described above, multidentate linkers can be employed [Nikitin, K. *Chem. Commun.* 2003, 282-283; Hu, J.; Mattern, D. L. *J. Org. Chem.* 2000, 65, 2277-2281; Yao, Y.; Tour, J. M. *J. Org. Chem.* 1999, 64, 1968-1971; Fox, M. A. et al. *Langmuir*, 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science*, 2001, 494, 1-20; Whitesell, J. K.; Chang, H. K. *Science*, 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl] methyl}phenyl,
1,1,1-tris[4-dihydroxyphosphorylmethyl)phenyl]methyl, and
4-{1,1,1-tris[4-(dihydroxyphosphorylmethyl)phenyl] methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to:

Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.

Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4'-yl, Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl, 4-[4-(3-hydroxypropyl)-1,7-dihydroxyhept-4-yl]biphen-4'-yl, etc.,
Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc.,
Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.
Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and
Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Active compounds of the invention can be provided as pharmaceutically acceptable salts. Such salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Active compounds of the invention include prodrugs of the compounds described herein. As noted above, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Utility.

The methods and intermediates described herein are useful for the synthesis of compounds of Formula I as described herein. Such compounds are useful per se or in further modified form (e.g., as a salt, metalated compound, conjugate or prodrug) for diagnostic and therapeutic purposes in like manner as other compounds described for photodynamic therapy, such as described in US Patent Application Publication No. 2004/0044197 to Pandey et al. and as set forth in further detail below.

Stability.

An advantage of the compounds of the present invention is their stability and absorption characteristics. Thus, the present invention provides a "neat" composition consisting of an active compound of the invention (e.g., compounds of Formula I, or the pharmaceutically acceptable salts, prodrugs, or conjugates thereof (e.g, with a targeting agent such as a protein, peptide or antibody)), wherein the composition has or is characterized by a peak Molar absorption coefficient in solution of at least 10,000, up to 300,000 $M^{-1}$ $cm^{-1}$ or more, at a wavelength between 700 and 1000 nanometers (it being understood that (a) the active compound must be placed into solution to determine its peak Molar absorption coefficient at the indicated wavelength; and (b) the compound may exhibit additional peaks outside of this range, or multiple peaks within this range).

In addition, the present invention provides compositions comprising or consisting essentially of an active compound of the invention (e.g., compounds of Formula I, or the pharmaceutically acceptable salts, prodrugs, or conjugates thereof (e.g, with a targeting agent such as a protein, peptide or antibody)) in a solvent. The amount of solvent is not critical and may comprise from 0.01 or 1 to 99 or 99.99 percent by weight of the composition. The composition has or is characterized by a peak Molar absorption coefficient in solution of at least 10,000, up to 300,000 $M^{-1}cm^{-1}$ or more, at a wavelength between 700 and 1000 nanometers. It will be appreciated that agitation may be required to break agglomerated particles back into solution prior to determining molar absorption, but that some level of agglomeration may actually be desired for practical use of the composition. Suitable solvents depend upon the particular compound and intended use for that compound, but include both organic solvents, aqueous solvents and combinations thereof.

The compositions, be they the bacteriochlorin compounds in "neat" form or the compounds mixed with a solvent, have or exhibit a loss of not more than 10, 15 or 20 percent by weight of the bacteriochlorin compound of the invention (due to degredation thereof) when stored in a sealed vessel (e.g., a flask ampoule or vial), at room temperature in the absence of ambient light for at least 3 or 4 months. Degredation can be determined by spectroscopy, thin-layer chromatography, NMR spectroscopy, and/or mass spectrometry, in accordance with known techniques.

2. Pharmaceutical Formulations.

Formulation of Pharmaceutical Compositions.

The pharmaceutical compositions provided herein contain therapeutically effective amounts of one or more of the compounds provided herein that are useful in the prevention, treatment, or amelioration of one or more of the symptoms of diseases or disorders associated with hyperproliferating tissue or neovascularization, or in which hyperproliferating tissue or neovascularization is implicated, in a pharmaceutically acceptable carrier. Diseases or disorders associated with hyperproliferating tissue or neovascularization include, but are not limited to, cancer, psoriasis, atherosclerosis, heart disease, and age-related macular degeneration. Pharmaceutical carriers suitable for administration of the compounds provided herein include any such carriers known to those skilled in the art to be suitable for the particular mode of administration.

Pharmaceutical compositions preferably exhibit the absorption characteristics and storage or stability characteristics described above.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier.

The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with hyperproliferating tissue or neovascularization or in which hyperproliferating tissue or neovascularization is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with hyperproliferating tissue or neovascularization or in which hyperproliferating tissue or neovascularization is implicated, as described herein.

In one embodiment, a therapeutically effective dosage should produce a serum concentration of active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN™, or dissolution in aqueous sodium bicarbonate.

Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Compositions for Oral Administration.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration.

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient. When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

3. Injectables, Solutions and Emulsions.

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticizednylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, xanthan gum, hydroxypropyl methylcellulose and polyvinylpyrrolidone. Emulsifying agents include Polysorbate 80 (TWEEN™ 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders.

Lyophilized powders, which can be reconstituted for administration as solutions, emulsions and other mixtures, can also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Compositions for Other Routes of Administration.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983; 6,261,595; 6,256,533; 6,167,301; 6,024,975; 6,010,715; 5,985,317; 5,983,134; 5,948,433 and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations.

The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

Liposomes.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Ligands.

In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, can be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Esherichia coli, Neisseria gonorrhosae, Neisseria meningitidis, Pneumococcus, Hemophilis influenzae* B, *Treponema pallidum*, Lyme disease, spirochetes, *Pseudomonas aeruginosa, Mycobacterium leprae, Brucella abortus, Mycobacterium tuberculosis*, Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis, Taenia saginata*, Anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Red virus, Polio virus, Dengue virus, Rubella virus, Murine leukemia virus, Antimycoplasmal MAbs such as those against *Acholeplasma Mycoplasma arthritidis, M. hyorhinis, M. orale, M. arginini, M. pneumonia*; etc.

Suitable MAbs have been developed against most of the micro-organisms (bacteria, viruses, protozoa, other parasites) responsible for the majority of infections in humans, and many have been used previously for in vitro diagnostic purposes. These antibodies, and newer MAbs that can be generated by conventional methods, are appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to *T. gondii*, the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating target tissue and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include F(ab')$_2$, F(ab)$_2$, Fab', Fab, Fv and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin.

A ligand or one member of a ligand-receptor binding pair can be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Conjugation to Ligands.

Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorin e via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein can also be conjugated to a ligand, such as an antibody, by using a coupling agent. Any bond which is capable of linking the components such that they are stable under physiological conditions for the time needed for administration and treatment is suitable, but covalent linkages are preferred. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies can be prepared by coupling the compound to targeting moieties by cleaving the ester on the "d" ring and coupling the compound via peptide linkages to the antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-5-acetyl-thioacetate (SATA), N-succinimidyl-3-(2-pyridyldi-thio)propionate (SPDP), ortho-phenylene-dimaleimide (o-PDM), and sulfosuccinimidyl 4-(N-maleimido-methyl)-cyclohexane-1-carboxylate (sulfo-SMCC). See, e.g., Karpovsky et al. J. Exp. Med. 160:1686 (1984); and Liu, M A et al., Proc. Natl. Acad. Sci. USA 82: 8648 (1985). Other methods include those described by Brennan et al. Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages O-90 to O-110 (1995, Pierce Chemical Co., 3747 N. Meridian Rd., Rockford Ill., 61105, U.S.A.), which catalog is hereby incorporated by reference.

For example, DCC is a useful coupling agent that can be used to promote coupling of the alcohol NHS to chlorin e6 in DMSO forming an activated ester which can be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NHS-esters and pyridyldithio groups, and produces cleavable cross-linking such that, upon further reaction, the agent is eliminated so the photosensitizer can be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in EPO 243,929 A2 (published Nov. 4, 1987).

Photosensitizers which contain carboxyl groups can be joined to lysine s-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together.

See the Pierce Catalog, and Merrifield, R. B. et al., Ciba Found Symp. 186: 5-20 (1994).

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which hyperproliferating tissue or neovascularization is implicated as a mediator or contributor to the symptoms or cause.

3. Methods of Use.

A. Methods of PDT, Diagnostic and Therapeutic Applications.

Briefly, the photosensitizing compound is generally administered to the subject before the target tissue, target composition or subject is subjected to illumination. The photosensitizing compound is administered as described elsewhere herein.

The dose of photosensitizing compound can be determined clinically. Depending on the photosensitizing compound used, an equivalent optimal therapeutic level will have to be established. A certain length of time is allowed to pass for the circulating or locally delivered photosensitizer to be taken up by the target tissue. The unbound photosensitizer is cleared from the circulation during this waiting period, or additional time can optionally be provided for clearing of the unbound compound from non-target tissue. The waiting period will be determined clinically and may vary from compound to compound.

At the conclusion of this waiting period, a laser light source or a non-laser light source (including but not limited to artificial light sources such as fluorescent or incandescent light, or natural light sources such as ambient sunlight) is used to activate the bound drug. The area of illumination is determined by the location and dimension of the pathologic region to be detected, diagnosed or treated. The duration of illumination period will depend on whether detection or treatment is being performed, and can be determined empirically. A total or cumulative period of time anywhere from between about 4 minutes and 72 hours can be used. In one embodiment, the illumination period is between about 60 minutes and 148 hours. In another embodiment, the illumination period is between about 2 hours and 24 hours.

Preferably, the total fluence or energy of the light used for irradiating, as measured in Joules, is between about 10 Joules and about 25,000 Joules; more preferably, between about 100 Joules and about 20,000 Joules; and most preferably, between about 500 Joules and about 10,000 Joules. Light of a wavelength and fluence sufficient to produce the desired effect is selected, whether for detection by fluorescence or for therapeutic treatment to destroy or impair a target tissue or target composition. Light having a wavelength corresponding at least in part with the characteristic light absorption wavelength of the photosensitizing agent is preferably used for irradiating the target issue.

The intensity or power of the light used is measured in watts, with each Joule equal to one watt-sec. Therefore, the intensity of the light used for irradiating in the present invention may be substantially less than 500 mW/cm$^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent.

In one embodiment of using compounds disclosed herein for photodynamic therapy, the compounds are injected into the mammal, e.g. human, to be diagnosed or treated. The level of injection is usually between about 0.1 and about 0.5 umol/kg of body weight. In the case of treatment, the area to be treated is exposed to light at the desired wavelength and energy, e.g. from about 10 to 200 J/cm$^2$. In the case of detection, fluorescence is determined upon exposure to light at a wavelength sufficient to cause the compound to fluoresce at a wavelength different than that used to illuminate the compound. The energy used in detection is sufficient to cause fluorescence and is usually significantly lower than is required for treatment.

Any one of the photosensitizing compounds disclosed herein or a pharmaceutically acceptable derivative thereof may be supplied in a kit along with instructions on conducting any of the methods disclosed herein. Instructions may be in any tangible form, such as printed paper, a computer disk that instructs a person how to conduct the method, a video cassette containing instructions on how to conduct the method, or computer memory that receives data from a remote location and illustrates or otherwise provides the instructions to a person (such as over the Internet). A person may be instructed in how to use the kit using any of the instructions above or by receiving instructions in a classroom or in the course of treating a patient using any of the methods disclosed herein, for example.

Additional examples and specific examples of methods of using compounds and compositions of the present invention include but are not limited to the following:

(i) Treatment of Opportunistic Infections.

Compounds, compositions and methods of the invention are useful for PDT of opportunistic infections, particularly of soft tissue. For antimicrobial treatment (via PDT) of infections, particularly wound infections, the infecting organism can include (as non limiting examples) *Staphylococcus aureus, Pseudomonas aeruginosa, Escherichia coli*. In nosocomial infections, *P. aeruginosa* is responsible for 8% of surgical-wound infections and 10% of bloodstream infections. In some embodiments the subjects are immunocompromised subjects, such as those afflicted with AIDS or undergoing treatment with immunosupressive agents.

(ii) Treatment of Burns.

Infections by *S. aureus* and gram-positive bacteria in general are particularly pronounced in burns (Lambrechts, 2005). The multidrug resistance of *S. aureus* presents significant medical challenges. In this regard, compounds, compositions and methods of the invention are useful for the treatment of opportunistic infections of burns.

(iii) Sepsis.

Compounds, compositions and methods of the invention are useful for the PDT treatment of subjects afflicted with opportunistic infections of *Vibrio vulnificus*. *V vulnificus*, a gram-negative bacterium, causes primary sepsis, wound infections, and gastrointestinal illness in humans.

(iv) Ulcers.

Compounds, compositions and methods of the invention are useful for PDT treatment of the bacterium that causes ulcers (*Helicobacter pylori*). In the clinic, treatment can be effected in any suitable manner, such as by insertion of a fiber optic cable (akin to an endoscope but with provisions for delivery of red or near-IR light) into the stomach or afflicted region.

(v) Periodontal Disease.

Compounds, compositions and methods of the invention are useful in PDT for the treatment of periodontal disease, including gingivitis. Periodontal disease is caused by the overgrowth of bacteria, such as the gram-negative anaerobe *Porphyromonas gingivalis*. As with many PDT treatments, targeting or solubilizing entities in conjunction with the photoactive species are essential for appropriate delivery of the photoactive species to the desired cells. The oral pathogens of interest for targeting include *Porphyromonas gingivalis, Actinobacillus actinomycetemcomitans, Bacteroides forsythus, Campylobacter rectus, Eikenella corrodens, Fusobacterium nucleatum* subsp. *Polymorphum, Actinomyces viscosus*, and the streptococci. For such applications the compounds or compositions of the invention can be topically applied (e.g., as a mouthwash or rinse) and then light administered with an external device, in-the-mouth instrument, or combination thereof.

(vi) Atherosclerosis.

Compounds, compositions and methods of the invention are useful in PDT to treat vulnerable atherosclerotic plaque. Without wishing to be bound to any particular theory, invading inflammatory macrophages are believed to secrete metalloproteinases that degrade a thin layer of collagen in the coronary arteries, resulting in thrombosis, which often is lethal (Demidova and Hamblin, 2004). Bacteriochlorins targeted to such inflammatory macrophages are useful for PDT of vulnerable plaque.

(vii) Cosmetic and Dermatologic Applications.

Compounds, compositions and methods of the invention are useful in PDT to treat a wide range of cosmetic dermatological problems, such as hair removal, treatment of psoriasis, or removal of skin discoloration. Ruby lasers are currently used for hair removal; in many laser treatments melanin is the photosensitized chromophore. Such treatments work reasonably well for fair-skinned individuals with dark hair. Compounds, compositions and methods of the invention can be used as near-IR sensitizers for hair removal, which enables targeting a chromophore with a more specific and sharp absorption band.

(viii) Acne.

Compounds, compositions and methods of the invention are useful in PDT to treat acne. Acne vulgaris is caused by *Propionibacterium acnes*, which infects the sebaceous gland; some 80% of young people are affected. Here again, the growing resistance of bacteria to antibiotic treatment is leading to an upsurge of acne that is difficult to treat. Current PDT treatments of acne typically rely on the addition of aminolevulinic acid, which in the hair follicle or sebaceous gland is converted to free base porphyrins. Compounds and compositions of the invention can be administered to subjects topically or parenterally (e.g., by subcutaneous injection) depending upon the particular condition.

(ix) Infectious Diseases.

Compounds, compositions and methods of the invention are useful in PDT to treat infectious diseases. For example, Cutaneous leishmaniasis and sub-cutaneous leishmaniasis, which occurs extensively in the Mediterranean and Mideast regions, is currently treated with arsenic-containing compounds. PDT has been used to reasonable effect recently, at least in one case, on a human patient. The use of compounds and compositions of the present invention are likewise useful, and potentially offer advantages such as ease of synthesis and better spectral absorption properties.

(x) Tissue Sealants.

Compounds, compositions and methods of the invention are useful in PDT as tissue sealants in subjects in need thereof. Light-activated tissue sealants are attractive for sealing wounds, bonding tissue, and closing defects in tissue There are many applications where sutures or staples are undesirable, and use of such mechanical methods of sealing often lead to infection and scarring.

(xi) Neoplastic Disease.

Compounds, compositions and methods of the invention are useful in PDT for treating neoplastic diseases or cancers, including skin cancer, lung cancer, colon cancer, breast cancer, prostate cancer, cervical cancer, ovarian cancer, basal cell carcinoma, leukemia, lymphoma, squamous cell carcinoma, melanoma, plaque-stage cutaneous T-cell lymphoma, and Kaposi sarcoma.

B. Imaging Enhancing Agents.

In addition to PDT, the compositions provided herein can be used as imaging enhancing agents in diagnostic imaging techniques, or for the labeling of target tissues or target compositions for diagnostic radiology. In the modern medical field, there are a variety of treatments including magnetic resonance imaging (MRI) for the diagnosis of diseases. Detection of cancer in its early stages should improve the ability to cure eliminate the cancerous tissue. Early diagnosis of precancerous regions and minute cancer are important subject matters in modern cancer treatments. MRI has emerged as a powerful tool in clinical settings because it is noninvasive and yields an accurate volume rendering of the subject. The image is created by imposing one or more orthogonal magnetic field gradients upon the subject or specimen while exciting nuclear spins with radio frequency pulses as in a typical nuclear magnetic resonance (NMR) experiment. After collection of data with a variety of gradient fields, deconvolusion yields a one, two, or three dimensional image of the specimen/subject. Typically, the image is based on the NMR signal from the protons of water where the signal intensity in a given volume element is a function of the water concentration and relaxation times. Local variation in there parameters provide the vivid contrast observed in MR images.

MRI contrast agents act by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast.

Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American 246: 78 (1982); Runge et al., Am. J. Radiol. 141: 1209 (1983). When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI image enhancing agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues (U.S. Pat. No. 5,059,415). Unfortunately, the relaxivity of Gd bound to antibodies has been found to be only slightly better than that of unbound Gd-DTPA (Paajanen et al., Magn. Reson. Med 13: 38-43 (1990)).

MRI is generally used to detect $^1H$ nuclei in the living body. However, MRI is capable of detecting NMR spectrums of other nuclear species, including $^{13}C$, $^{15}N$, $^{31}P$, and $^{19}F$. The $^{19}F$ is not abundant in the living body. By incorporating isotopes useful in MRI, such as $^{13}C$, $^{15}N$, $^{31}P$, or $^{19}F$, and particularly $^{19}F$ in the compositions provided herein and administering to a subject, the compounds provided herein would accumulate in target tissue, and subsequent MR imaging would produce NMR data with enhanced signal from the targeted tissue or target compositions due to the presence of the accumulated compound with the MRI recognizable isotope, such as $^{19}F$. Thus, the disclosed compounds can be used as image enhancing agents and provide labeling of specific target tissues or target compositions for diagnostic radiology, including MRI.

C. Detecting Target Tissue or Target Compositions.

In addition to PDT, the compositions provided herein can be used to detect target cells, target tissue, or target compositions in a subject. When the compounds provided herein are to be used for detection of target tissue or target composition, the compounds are introduced into the subject and sufficient time is allowed for the compounds to accumulate in the target tissue or to become associated with the target composition. The area of treatment is then irradiated, generally using light of an energy sufficient to cause fluorescence of the compound, and the energy used is usually significantly lower than is required for photodynamic therapy treatment. Fluorescence is determined upon exposure to light at the desired wavelength, and the amount of fluorescence can be correlated to the presence of the compound, qualitatively or quantitatively, by methods known in the art.

D. Diagnosing an Infecting Agent.

The compositions provided herein can be used to diagnose the presence of an infecting agent, or the identity of an infecting agent in a subject. The compounds provided herein can be conjugated to one or more ligands specific for an infecting agent, such as an antibody or antibody fragment, that selectively associates with the infecting agent, and after allowing sufficient time for the targeted compound to associate with the infecting agent and to clear from non-target tissue, the compound can be visualized, such as by exposing to light of an energy sufficient to cause fluorescence of the compound, or by imaging using diagnostic radiology, including MRI. By way of example, any one of the compounds provided herein can be conjugated to an antibody that is targeted against a suitable *Helicobacter pylori* antigen, and formulated into a pharmaceutical preparation that, when introduced into a subject, releases the conjugated compound to a gastric mucus/epithelial layer where the bacterium is found. After sufficient time for the compound to selectively associate with the target infecting agent, and for any unbound compound to clear from non-target tissue, the subject can be examined to determine whether any *Helicobacter pylori* is present. This can be done by MRI to detect accumulated compound because of the presence of $^{19}F$ substituents, for example, or by irradiating the suspect target area with light of an energy sufficient to cause fluorescence of the compound, such as by using fiberoptics, and detecting any fluorescence of the targeted compound.

3. Solar Cells, Light Harvesting Rods and Light Harvesting Arrays.

Bacteriochlorins of Formula I herein may be used as chromophores (also referred to as photosensitizers or simply sensitizers) in solar cells, including but not limited to high surface area colloidal semiconductor film solar cells (Gratzel cells), as described in, for example, U.S. Pat. Nos. 5,441,827; 6,420,648; 6,933,436; 6,924,427; 6,913,713; 6,900,382; 6,858,158; and 6,706,963.

Bacteriochlorins of Formula I may be used as chromophores in the light harvesting rods described in U.S. Pat. Nos. 6,407,330 and 6,420,648 (incorporated herein by reference). The light harvesting rod may comprise one or more bacteriochlorins of Formula I coupled to one or two adjacent chromophores depending upon the position thereof in the light harvesting rod. Such light harvesting rods may be utilized to produce light harvesting arrays as described in U.S. Pat. No. 6,420,648 and solar cells as described in U.S. Pat. No. 6,407,330.

4. Flow Cytometry.

Flow cytometry is known and described in, for example, U.S. Pat. Nos. 5,167; 5,915,925; 6,248,590; 6,589,792; and 6,890,487. In some embodiments the particle being detected, such as a cell, is labelled with a luminescent compound such as a phosphor or fluorophore for detection. Labelling can be carried out by any suitable technique such as coupling the luminescent compound to another compound such as an antibody which in turn specifically binds to the particle or cell, by uptake or internalization of the luminescent compound into the cell or particle, by non-specific adsorption of the luminescent compound to the cell or particle, etc. The bacteriochlorins described herein are useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

5. Information Storage Devices.

Bacteriochlorins of the invention are also useful immobilized to a substrate for making charge storage molecules and information storage devices containing the same, either individually or as linked polymers thereof, either optionally including additional compounds to add additional oxidation states. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al. The bacteriochlorins of the invention may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the following non-limiting Examples.

Experimental

Here we extend the de novo route to create stable, tailorable analogues of the fundamental bacterio-13$^1$-oxophorbine and bacteriochlorin-13,15-dicarboximide macrocyclic skeletons (Chart 1, panel C).[52] The synthesis and spectroscopic analysis of such synthetic macrocycles is essential for understanding the structural features that underpin the characteristic spectral properties of the naturally occurring bacteriochlorophylls.

Results and Discussion

I. Retrosynthetic Analysis.

An approach to stable bacterio-13$^1$-oxophorbine and bacteriochlorin-13,15-dicarboximide macrocycles is outlined in Scheme 1. The bacteriochlorin macrocycle is created upon acid-catalyzed condensation of a dihydrodipyrrin-acetal. Subsequent derivatization to install the annulated rings builds on the strategies we have developed in chlorin chemistry for the preparation of the 13$^1$-oxophorbine[53] and chlorin-imide[54] frameworks. Thus, the construction of both rings relies on regioselective 15-bromination followed by intramolecular Pd-mediated ring closure. Access to the former requires the presence of a 13-acetyl group for α-arylation[55] whereas the latter requires a 13-ester group for carbonylation and imidation.

Scheme 1. Retrosunthetic analysis of stable bacteriochlorins containing a fifth ring.

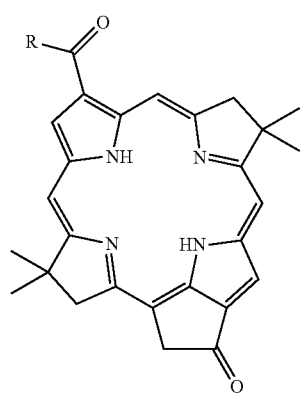

a bacterio-13$^1$-oxophorbine

R = Me

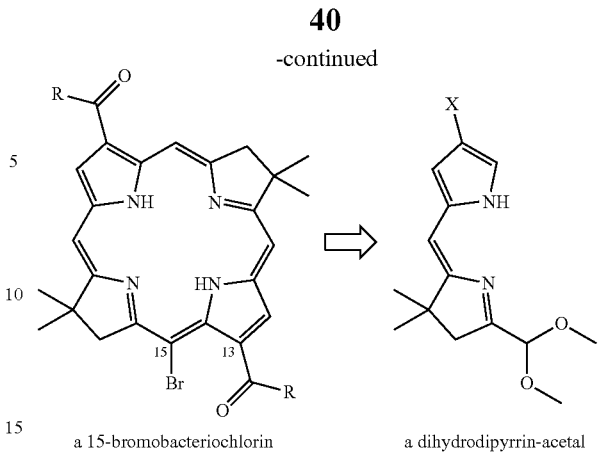

a 15-bromobacteriochlorin    a dihydrodipyrrin-acetal

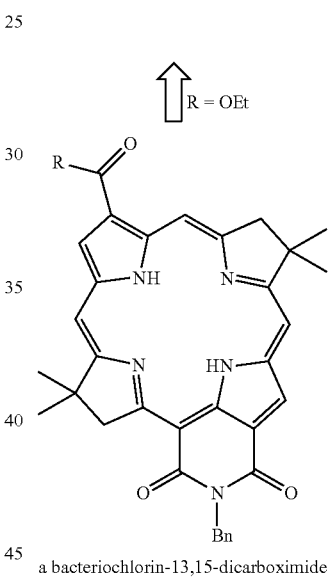

R = OEt a bacteriochlorin-13,15-dicarboximide

II. Regioselective 15-Bromination.

A number of 5-methoxy substituted bacteriochlorins are known to undergo regioselective 15-bromination.[46,47] Therefore, an initial approach to the target bacteriochlorin-13$^1$-oxophorbine was to convert the 3,13-dibromo-5-methoxy-bacteriochlorin MeOBC-Br to the 3,13-diacetyl-5-methoxybacteriochlorin MeOBC-A followed by 15-bromination and Pd-mediated ring closure. However, the presence of 3,13-diacetyl groups in MeOBC-A caused loss of regioselectivity during the bromination step (Scheme 2). This result was not entirely surprising, given that the same loss of regioselectivity was observed in the case of a bacteriochlorin bearing 3,13-diester groups.[46] MeOBC-A was treated with ethylene glycol and TMSCl[56] to form the ketal-protected analogue MeOBC-K in an attempt to mitigate the electron-withdrawing effect of the acetyl group, but again regioselective bromination was not obtained (Scheme 2).

Scheme 2. Attempted synthesis of a 15-bromo-3,13-diacetylbacteriochlorin.

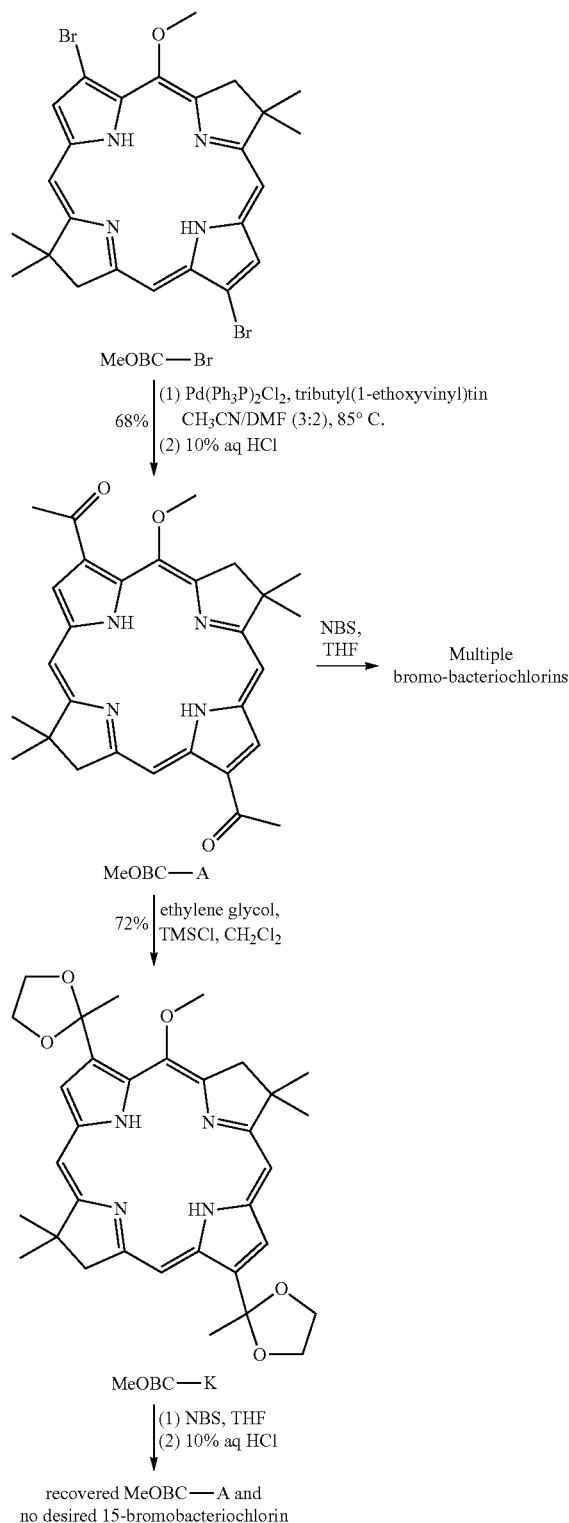

Scheme 3. Prior demonstration of regioselective 15-bromination.

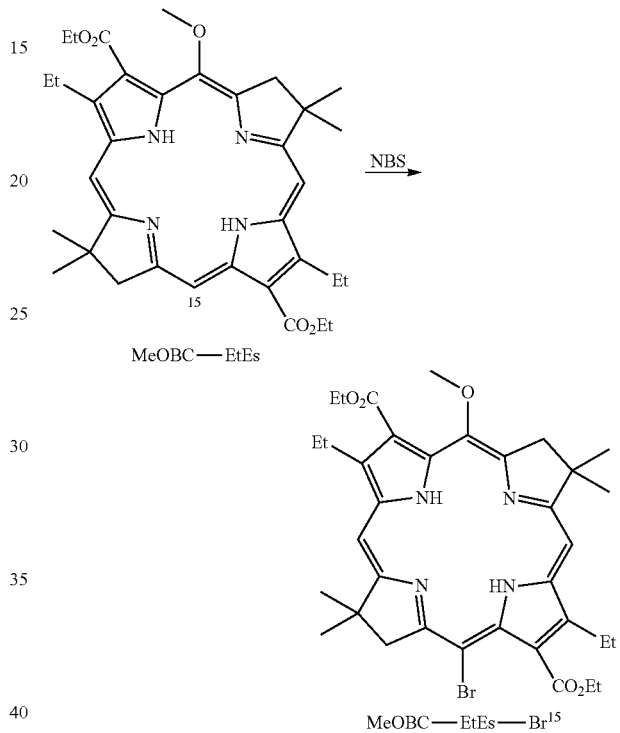

To effect regioselective 15-bromination in the presence of electron-withdrawing substituents (e.g., acetyl or ester), the remaining β-pyrrolic positions need to be blocked, which can be achieved with alkyl groups. Indeed, we have previously reported the regioselective bromination of 2,12-diethyl-3,13-diethoxycarbonyl-5-methoxybacteriochlorin MeOBC-EtEs to give the key precursor to the bacteriochlorin-13,15-dicarboximides, the 15-bromobacteriochlorin MeOBC-EtEs-Br[15] (Scheme 3).[46] The use of bacteriochlorins wherein the three β-pyrrole sites that are not integral to ring E are substituted (i.e., positions 2, 3, and 12) proved to be an essential requirement for the approaches developed here to introduce the two ring E motifs.

III. Synthesis.

The target bacterio-13[1]-oxophorbine was pursued via the intermediacy of dihydrodipyrrin-acetal 1, which bears bromo and methyl substituents at the β-pyrrolic positions (Scheme 4). Upon conversion to the bacteriochlorin, the bromo substituent provides a synthetic handle for introduction of the acetyl group, and the methyl group prevents bromination at the pyrrole positions during 15-bromination. Preparation of 1 closely follows the optimized condition for a dihydrodipyrrin-acetal lacking the methyl group on the pyrrole.[50] The synthesis of 1 entails formation of 3-methyl-pyrrole-2-carboxaldehyde (2) by photochemical rearrangement of 4-picoline-N-oxide,[57] bromination to give bromopyrrole 3, tosyl-protection of the pyrrole (3-Ts), nitro-aldol (Henry) condensation followed by reduction to give the 2-(2-nitroethyl)pyrrole 4-Ts, Michael addition with the α,β-unsaturated ketone-acetal 5[44] to give the nitrohexanone-pyrrole 6-Ts, removal of the tosyl group (6-H), and McMurry-type ring closure to 1. The presence of the tosyl group was necessary to increase the stability of key intermediates.

Dihydrodipyrrin-acetal 1 was subjected to self-condensation conditions optimized for selective formation of either the 5-methoxybacteriochlorin or the 5-unsubstituted-bacteriochlorin.[44,46] Thus, self-condensation of 1 in CH$_2$Cl$_2$ containing TMSOTf/2,6-DTBP gave MeOBC-MeBr; self-condensation in CH$_3$CN containing BF$_3$·OEt$_2$ gave HBC-MeBr. Stille coupling of each bacteriochlorin with tributyl(1-ethoxyvinyl)tin[58] followed by acidic hydrolysis gave diacetylbacteriochlorins MeOBC-MeA and HBC-MeA. (Note: The reactions were carried out in THF for 23 h[45] instead of DMF/CH$_3$CN[59] for 2 h; the latter afforded mono-reacted bromo-acetylbacteriochlorin.) 15-Bromination of 5-methoxybacteriochlorin MeOBC-MeA proceeded smoothly to give MeOBC-MeA-Br[15], whereas treatment of 5-unsubstituted-bacteriochlorin HBC-MeA with 1 equiv of NBS gave the 5,15-dibromobacteriochlorin BC-MeA-Br[5,15] as the major product. Nonetheless, Pd-mediated intramolecular α-arylation of MeOBC-MeA-Br[15] created ring E and thereby completed the synthesis of the 5-methoxybacterio-13[1]-oxophorbine MeOBOP (Scheme 5). Attempted double cyclization of BC-MeA-Br[5,15] to give the bacteriochlorin-3[1],13[1]-dioxophorbine was unsuccessful.

Scheme 4. Synthesis of a bromo-dihydrodipyrrin-acetal.

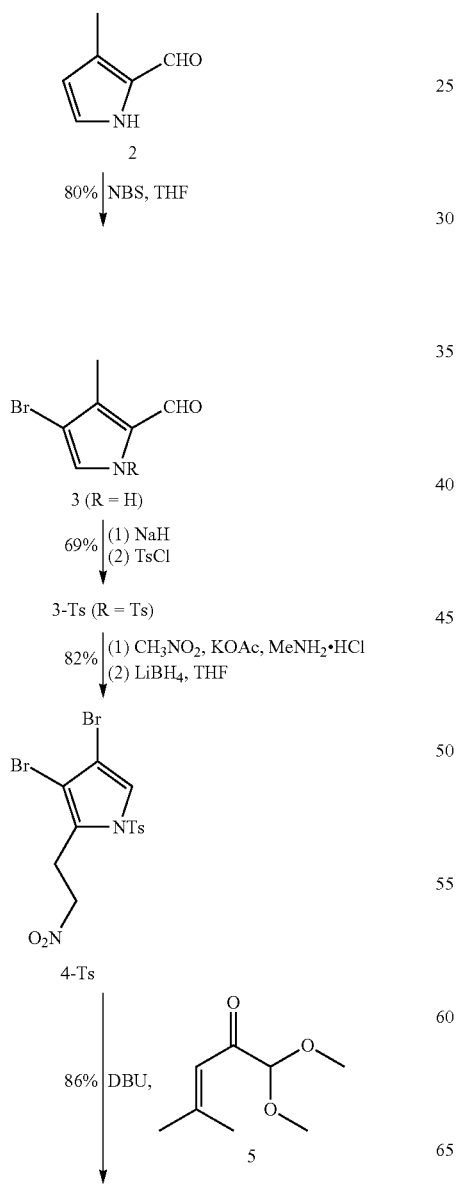

Scheme 5. Synthesis of a bacterio-13[1]-oxophorbine.

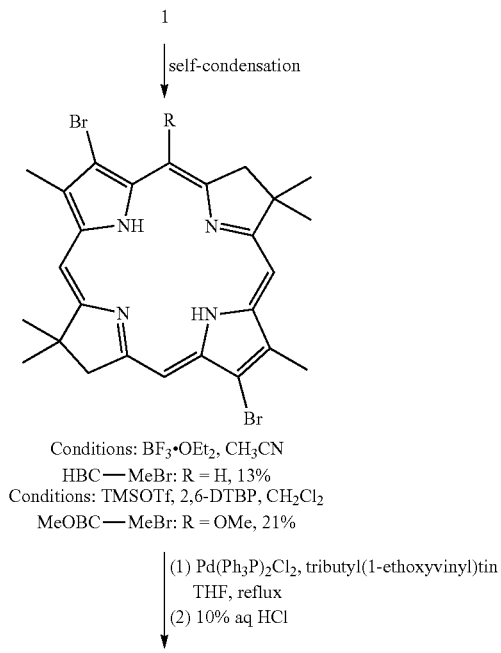

Conditions: BF$_3$·OEt$_2$, CH$_3$CN
HBC—MeBr: R = H, 13%
Conditions: TMSOTf, 2,6-DTBP, CH$_2$Cl$_2$
MeOBC—MeBr: R = OMe, 21%

(1) Pd(Ph$_3$P)$_2$Cl$_2$, tributyl(1-ethoxyvinyl)tin
    THF, reflux
(2) 10% aq HCl -continued

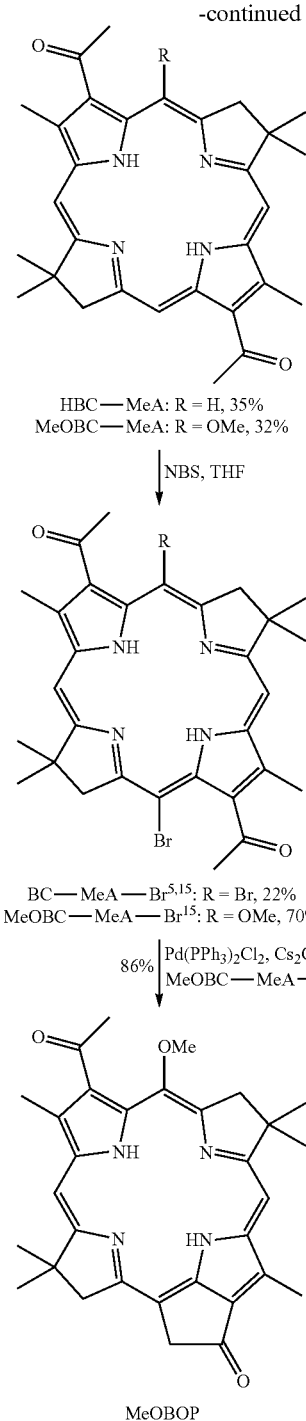

HBC—MeA: R = H, 35%
MeOBC—MeA: R = OMe, 32%

↓ NBS, THF

BC—MeA—Br[5,15]: R = Br, 22%
MeOBC—MeA—Br[15]: R = OMe, 70%

86% ↓ Pd(PPh$_3$)$_2$Cl$_2$, Cs$_2$CO$_3$, toluene
MeOBC—MeA—Br[15] only

MeOBOP ring closure resulted in the bacteriochlorin-13,15-dicarboximide MeOBC-I or HBC-I, respectively (Scheme 6).

Scheme 6. Synthesis of a bacteriochlorin-13,15-dicarboximide.

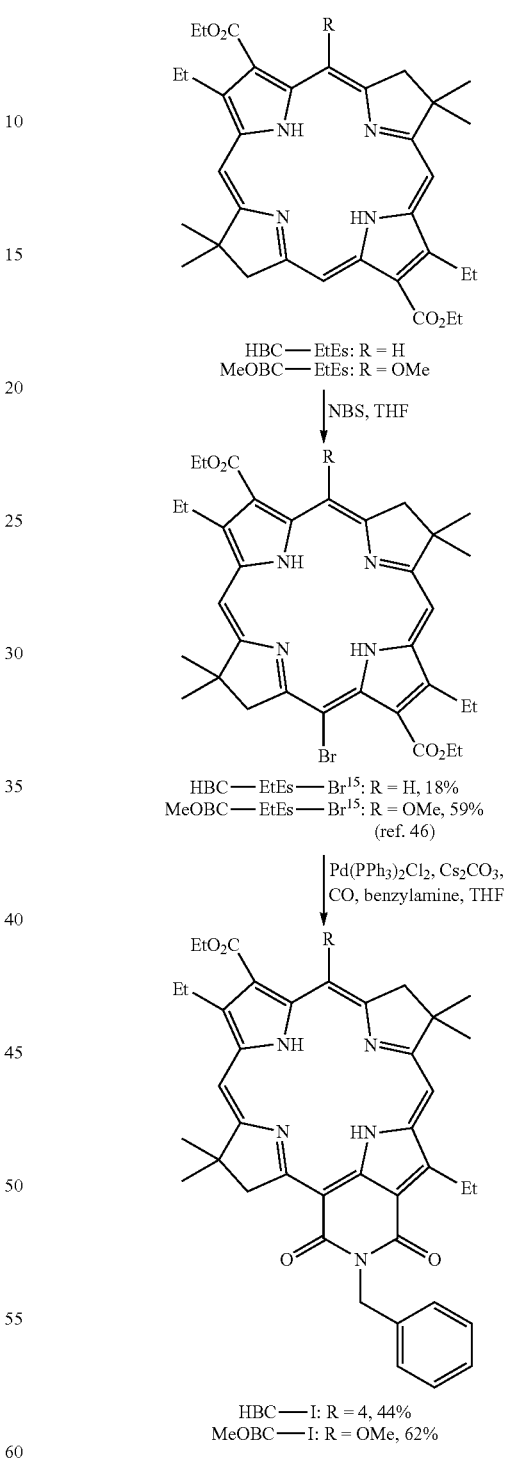

HBC—EtEs: R = H
MeOBC—EtEs: R = OMe

↓ NBS, THF

HBC—EtEs—Br[15]: R = H, 18%
MeOBC—EtEs—Br[15]: R = OMe, 59%
(ref. 46)

↓ Pd(PPh$_3$)$_2$Cl$_2$, Cs$_2$CO$_3$,
CO, benzylamine, THF

HBC—I: R = 4, 44%
MeOBC—I: R = OMe, 62%

For the synthesis of bacteriochlorin-13,15-dicarboximides, the known diester-bacteriochlorins[46] MeOBC-EtEs and HBC-EtEs were subjected to bromination. As before (Scheme 3), the bromination of 5-methoxybacteriochlorin MeOBC-EtEs proceeded smoothly to give the 15-bromobacteriochlorin MeOBC-EtEs-Br[15].[46] On the other hand, HBC-EtEs gave predominantly the 5,15-dibrominated product; however, the mono-brominated HBC-EtEs-Br[15] was isolated in sufficient quantities to complete the synthesis. Treatment of MeOBC-EtEs-Br[15] or HBC-EtEs-Br[15] in the presence of benzylamine to one-flask Pd-mediated carbamoylation and IV. Structural Characterization.

The bacteriochlorins were characterized by $^1$H NMR spectroscopy, IR spectroscopy, high resolution mass spectrometry (ESI-MS), absorption spectroscopy and fluorescence spectroscopy. We first consider the $^1$H NMR data. In general, a bacteriochlorin that has $C_{2h}$ symmetry (such as the H-BCtype macrocycles lacking the fifth ring or the 15-bromo substituent) exhibits a relatively simple $^1$H NMR spectrum. Introduction of a single substituent (e.g., 5-methoxy, 15-bromo or ring E) results in $C_s$ symmetry whereupon a number of otherwise identical structural elements in the respective A,C and B,D rings become magnetically non-equivalent and split into distinct signals. The non-equivalent entities include the two pyrrolic N—H protons, the pair of geminal dimethyl groups, the CH$_2$ group in each of the two pyrroline rings, and any β-pyrrolic substituents (e.g., methyl unit of the acetyl group in MeOBC-MeA). The synthetic bacteriochlorins synthesized to date typically exhibit a broad upfield peak in the region δ −2.40-0.12 ppm (pyrrolic N—H protons), a singlet between δ 1.81-2.02 ppm (geminal dimethyl groups), and a singlet between δ 4.30-4.50 ppm (pyrroline CH$_2$ groups). The $^1$H NMR signal for the 5-methoxy group generally resonates in the region δ 3.68-4.48 ppm.[44-46]

The $^1$H NMR spectrum of bacterio-13$^1$-oxophorbine MeOBOP displays the aforementioned features characteristic of bacteriochlorins with $C_s$ symmetry. In addition, the two protons at the 13$^2$-position (ring E) resonate as a singlet at δ 4.88 ppm, to be compared with the ABX pattern of the diastereotopic 13$^2$-protons of bacteriopyro-13$^1$-oxophorbines.[3,29,36,60] The chemical shift range is comparable to those of bacteriochlorophyll a derivatives (δ 4.76-5.31 ppm) and synthetic chlorophyll analogues (13$^1$-oxophorbines, δ 5.03-5.16 ppm).[53,59]

The bacteriochlorin-13,15-dicarboximides MeOBC-I and HBC-I also display $^1$H NMR spectral features characteristic of bacteriochlorins with $C_s$ symmetry. The $^1$H NMR spectra of MeOBC-I and HBC-I also provide information on the formation of the imide and/or isoimide ring, which are ever-present possibilities in the imidation process. In chlorin chemistry, the 13-ester-15-bromochlorin gave exclusively the chlorin-imide, whereas imide and isoimide mixtures were sometimes observed upon reaction of the 13-carbamoyl-15-bromochlorin.[54] A convenient method for distinguishing the two isomers relied on the chemical shift of the methylene protons of the N-benzyl (iso)imide: δ 5.6 ppm for the chlorin-imides versus 5.2 ppm for the corresponding chlorin-isoimides.[54] In the work reported herein, MeOBC-I and HBC-I were each obtained from the corresponding 13-ester-15-bromobacteriochlorin, and the benzylic protons of MeOBC-I and HBC-I resonated at δ 5.67 and 5.68 ppm, respectively. Such data by analogy with the chlorins are consistent with the formation of bacteriochlorin-imides.

The IR spectrum of MeOBOP shows carbonyl stretching bands at 1687 and 1630 cm$^{-1}$, along with bands at 2918-2954 cm$^{-1}$ (C—H) and 3435 cm$^{-1}$ (N—H). In comparison, the carbonyl stretch of a bacteriochlorin in a dyad (bacteriopyropheophorbide-pyromellitimide) occurs at 1695 cm$^{-1}$,[3] whereas that of a zinc chelate of a bacterio-13$^1$-oxophorbine appeared at 1682 cm$^{-1}$.[61] The carbonyl stretch for a variety of methylpyropheophorbides (chlorins) occurs in the region 1650-1699 cm$^{-1}$.[62,63] Tamiaki has used IR extensively to identify hydrogen-bonding with hydroporphyrin carbonyl groups in supramolecular assemblies.[61,63] The IR spectra of MeOBC-I and HBC-I show carbonyl stretching bands in the range of 1647-1682 cm$^{-1}$, along with bands in the region 2848-2959 cm$^{-1}$ (C—H) and 3386-3435 cm$^{-1}$ (N—H). To our knowledge, IR data have not been reported for other bacteriochlorin-imides.

V. Absorption Spectra.

The annulated bacteriochlorins prepared herein exhibit characteristic bacteriochlorin absorption spectra,[1] with near-ultraviolet (Soret or B) bands, a long-wavelength feature, the $Q_y(0,0)$ band, in the near-infrared region of comparable peak intensity, and the weaker $Q_x$ bands in the intervening region (500-600 nm). The position of the long wavelength absorption band of a photochemically active species is of central importance, defining not only the spectral region where absorption occurs but also the energy of the lowest singlet excited-state, which dominates key photophysical properties. These properties include fluorescence and, for the native bacteriochlorophylls, the energy- and electron-transfer reactions of photosynthesis.

Prior studies with synthetic bacteriochlorins have shown that the position of the $Q_y(0,0)$ band could be tuned from 707 nm to 792 nm (typically measured in toluene).[44-46,51] The synthetic bacterio-13$^1$-oxophorbine MeOBOP (733 nm) absorbs in this range, to be compared with that of methyl bacteriopyropheophorbide a (754 nm in CH$_2$Cl$_2$).[29] Bacteriopheophytin a (BPh-a), which differs from methyl bacteriopyropheophorbide a owing to the presence of a 13$^2$-methoxycarbonyl group and a long alkyl ester chain, also absorbs at 750-760 nm in hydrocarbon solvents.[64,65] The bacteriochlorin-imides MeOBC-I (793 nm) and HBC-I (818 nm) exhibit $Q_y(0,0)$ bands that extend further into the near infrared. The $Q_y(0,0)$ band of bacteriochlorin-imides derived from bacteriochlorophyll a occurs in the same spectral range (800-830 nm).[32,33,36]

The spectra of MeOBOP, MeOBC-I and HBC-I in toluene are shown in FIG. 1. The $Q_y(0,0)$ positions are listed in Table 1 along with those of a number of bacteriochlorin benchmarks that lack the annulated ring E. Reference molecules for MeOBOP include a set of 3,13-diacetylbacteriochlorins: MeOBC-MeA (743 nm), MeOBC-A (740 nm), HBC-MeA (766 nm) and HBC-A (768 nm). The first three of these 3,13-diacetylbacteriochlorins were prepared here (Schemes 2 and 5) whereas HBC-A (Chart 2) was synthesized previously.[45] Comparison among the four 3,13-diacetylbacteriochlorins shows that (1) the 5-methoxy group results in an average 25-nm hypsochromic shift in the $Q_y(0,0)$ position, and (2) the 2,12-dimethyl groups have little (<3 nm) effect on the $Q_y(0,0)$ position. The first point, regarding the 5-methoxy group, is also made upon comparison of the $Q_y(0,0)$ positions of bacteriochlorins MeOBC-EtEs (739 nm) and HBC-EtEs (761 nm).[46] The latter two compounds (Scheme 6) serve as benchmarks for the two bacteriochlorin-imides (MeOBC-I and HBC-I): the benchmarks contain the 2,12-diethyl and 3-ester groups but lack the 13,15-dicarboximide moiety. The $Q_y(0,0)$ position for MeOBC-I (793 nm) and HBC-I (818 nm), like the three pairs of bacteriochlorins noted above, shows a 25-nm hypsochromic shift due to the 5-methoxy group. Interestingly, the impact of the 5-methoxy group is diminished in bacteriochlorins that lack a carbonyl moiety (acetyl, ester, imide) at the 3,13-positions. This point is seen upon comparison of the $Q_y(0,0)$ positions of bacteriochlorins MeOBC (709 nm)[46] and HBC (713 nm)[45] that bear one or no substituents, respectively, other than the geminal dimethyl groups (Chart 2).

Chart 2. Benchmark bacteriochlorins prepared previously.[45]

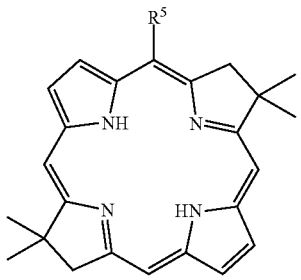

HBC, $R^5$ = H
MeOBC, $R^5$ = OMe

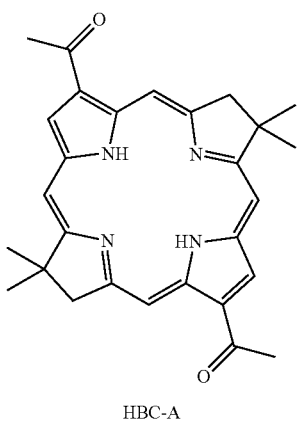

HBC-A

VI. Fluorescence Spectra, Quantum Yields, and Singlet Excited-State Lifetimes.

The fluorescence spectra of MeOBOP, MeOBC-I and HBC-I in toluene are shown in FIG. 1 (dotted lines). Each fluorescence spectrum is dominated by the $Q_y(0,0)$ band, which lies ~5 nm to longer wavelength than the corresponding $Q_y(0,0)$ absorption feature. The same is generally true for the benchmark bacteriochlorins listed in Table 1; exceptions include HBC-EtEs and MeOBC-EtEs, which show larger (~15 nm) Stokes shifts, suggesting greater changes in structure or solvent interactions upon photoexcitation.

The bathochromic shift of the $Q_y(0,0)$ band of MeOBOP, MeOBC-I and HBC-I (733 nm, 793 nm, 818 nm) is accompanied by a decrease in the fluorescence yield (0.19, 0.052, 0.036) and shortening of the singlet excited-state lifetime (4.6 ns, 2.2 ns, 1.9 ns). The same is true of the benchmark bacteriochlorins. These data are plotted in FIGS. 2C and D and listed in Table 1. For comparison, the average singlet excited-state lifetime of bacteriopheophytin a is 2.0-2.7 ns and has a $Q_y(0,0)$ band at 750-760 nm in organic solvents (Table 1).[64,65] Thus, the two synthetic bacteriochlorin-imides absorb at significantly longer wavelengths (by ~40 and ~70 nm) than the natural pigment and yet have comparable excited-state lifetime.

TABLE 1

Photophysical Properties of Bacteriochlorin Compounds.[a]

| Compound | Cmpd code for FIG. 2 | $\lambda_{Q_y}$ abs (nm) | $\lambda_{Q_y}$ em (nm) | $\lambda_{Q_y}/I_B$[b] | $\Phi_f$[c] | $\tau_s$ (ns)[d] | HOMO-LUMO (eV)[e] | HOMO-1-LUMO+1 (eV)[f] |
|---|---|---|---|---|---|---|---|---|
| Targets: | | | | | | | | |
| HBC-I | a | 818 | 823 | 1.3 | 0.036 | 1.9 | 1.92 | 4.01 |
| MeOBC-I | b | 793 | 798 | 1.0 | 0.052 | 2.2 | 2.02 | 3.92 |
| MeOBOP | h | 733 | 739 | 0.93 | 0.19 | 4.6 | 2.18 | 3.86 |
| Benchmarks: | | | | | | | | |
| HBC | i | 713 | 716 | 0.85 | 0.17 | 4.0 | 2.26 | 4.06 |
| HBC-A | c | 768 | 771 | 1.2 | 0.11 | 2.9 | 2.05 | 3.95 |
| HBC-MeA | | 766 | | | | | 2.02 | 3.94 |
| HBC-EtEs | d | 761 | 775 | 0.94 | 0.14 | 3.3 | 2.10 | 3.98 |
| MeOBC | j | 709 | 711 | 0.87 | 0.25 | 5.0 | 2.28 | 3.98 |
| MeOBC-A | f | 740 | 747 | 0.96 | 0.14 | 3.8 | 2.14 | 3.88 |
| MeOBC-MeA | e | 743 | 749 | 0.95 | 0.13 | 3.4 | 2.14 | 3.87 |
| MeOBC-EtEs | g | 739 | 749 | 1.1 | 0.17 | 4.3 | 2.16 | 3.91 |
| BPh-a[g] | | 758 | 768 | 0.69 | 0.10 | 2.7 | 2.03[h] | 3.89[h] |

TABLE 1-continued

Photophysical Properties of Bacteriochlorin Compounds.[a]

| Compound | Cmpd code for FIG. 2 | $\lambda_{Q_y}$ abs (nm) | $\lambda_{Q_y}$ em (nm) | $\lambda_{Q_y}/I_B$[b] | $\Phi_f$[c] | $\tau_s$ (ns)[d] | HOMO-LUMO (eV)[e] | HOMO-1-LUMO+1 (eV)[f] |
|---|---|---|---|---|---|---|---|---|
| Fictive: | | | | | | | | |
| MeOBC-MeAMe[15] | | | | | | | 2.17 | 3.80 |

[a]In toluene at room temperature unless noted otherwise.
[b]Ratio of the peak intensities of the $Q_y(0, 0)$ and B bands.
[c]Fluorescence quantum yield (error ± 7%).
[d]Lifetime of the lowest singlet excited state measured using fluorescence techniques (error ± 7%). Values for several of the benchmark compounds were reported in ref. 45,
[e]Energy gap between the LUMO and HOMO orbitals.
[f]Energy gap between the LUMO + 1 and HOMO-1 orbitals.
[g]Values are in toluene. The values in ethanol are $\lambda_{abs}$ = 750 nm, $\lambda_{em}$ = 768 nm, $I_{Q_y}/I_B$ = 0.39, $\Phi_f$ = 0.081, and $\tau_s$ = 2.3 ns. A value of $\tau_s$ = 2.0 ns in acetone/methanol 7:3 was found in ref 65.
[h]DFT calculations were performed with the truncated phytyl tail —CH$_2$CH═C(CH$_3$)(CH$_2$CH$_3$).

VII. Frontier Molecular Orbitals and Electronic Properties.

The energies and electron-density distributions of the frontier molecular orbitals (MOs) of the bacterio-13[1]-oxophorbine, bacteriochlorin-imides, and benchmark compounds were obtained from density functional theory (DFT) calculations. Such methods were also applied to the fictive bacteriochlorin MeOBC-MeAMe[15] (Chart 3), which differs from the benchmark compound MeOBC-MeA in the addition of a 15-methyl substituent. Examination of MeOBC-MeAMe[15] provides deeper insight into the origin of the effects caused by the formation of the fifth ring.

Chart 3.
Fictive bacteriochlorin for which DFT calculations were performed.

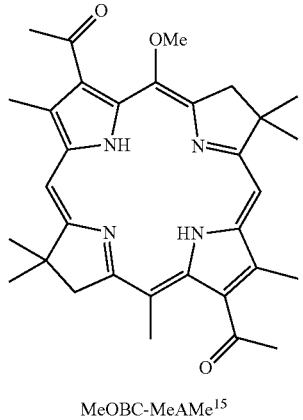

MeOBC-MeAMe[15]

The key results of the DFT calculations for MeOBOP, MeOBC-I, HBC-I and representative benchmark synthetic and fictive compounds are summarized in FIG. 2. This figure shows the characteristics of the four frontier orbitals: the highest occupied molecular orbital (HOMO), the lowest unoccupied molecular orbital (LUMO), the HOMO-1, and LUMO+1. The energies of these MOs are plotted as a function of the $Q_y(0,0)$ absorption-band energy/wavelength in FIG. 2A, and analogous plots for the HOMO-LUMO energy gap and HOMO-1-LUMO+1 energy gap are shown in FIG. 2B. In each of these plots, the data for the key target compounds (MeOBOP, MeOBC-I and HBC-I) are given by closed symbols and those for the benchmark bacteriochlorins by open symbols. The values for the HOMO-LUMO and HOMO-1-LUMO+1 energy gaps for the various compounds are listed in Table 1. These two energy gaps are relevant to the spectral analysis given below.

The salient points from the DFT calculations and the relationship to the observed spectral properties are as follows:

(1) The slopes of the trend lines given in FIG. 2A show that the LUMO (m=3.2) is more strongly connected with the wavelength/energy of the $Q_y(0,0)$ absorption band than are the HOMO (m=1.8), LUMO+1 (m=2.3) and HOMO-1 (m=2.4). These differences can be traced to the generally greater electron density in the LUMO at the substituent sites (Table 3). The most important sites in this regard are the 3,13-positions of the carbonyl substituents (acetyl, ester, imide) of MeOBOP, MeOBC-I, HBC-I and the benchmark bacteriochlorins. These sites (and the 2,12-positions) are on the molecular y-axis, which is the axis on which the $Q_y$ optical transition is polarized.

(2) In Gouterman's four-orbital model,[66,67] the position of the $Q_y(0,0)$ absorption band depends on the average value of the HOMO-LUMO energy gap and the HOMO-1-LUMO+1 energy gap. Because of the trends in the individual molecular orbitals described above and shown in FIG. 2A, there is a much greater variation in the HOMO-LUMO energy gap versus the HOMO-1-LUMO+1 energy gap for MeOBOP, MeOBC-I, HBC-I and the benchmark bacteriochlorins (Table 1). The consequence is a much greater magnitude of the slope of the trend line for the HOMO-LUMO energy gap (m=1.4) versus the HOMO-1-LUMO+1 energy gap (m=−0.05) plotted against the $Q_y(0,0)$ wavelength/energy (FIG. 2B). Consequently, the wavelength/position of the $Q_y(0,0)$ band is dominated by the HOMO-LUMO energy gap for the bacterio-13[1]-oxophorbine, bacteriochlorin-imides, and bacteriochlorins described here. In turn, following the findings given in point (1), the spectral position is dictated much more strongly by the dependence of the LUMO than the HOMO on the macrocycle-substituent pattern for these molecules.

(3) The DFT calculations reproduce the effect of the 5-methoxy group on the position of the $Q_y(0,0)$ wavelength/energy. This can be seen by comparing the value for the $Q_y(0,0)$ wavelength and the HOMO-LUMO energy gap for the following pairs of 3,13-carbonyl-containing (acetyl, ester, imide) compounds (Table 1): MeOBC-I (793 nm, 2.02 eV) versus HBC-I (818 nm, 1.92 eV); MeOBC-EtEs (739 nm, 2.16 eV) versus HBC-EtEs (761 nm, 2.10 eV); MeOBC-MeA (743 nm, 2.14 eV) versus HBC-MeA (766 nm, 2.02 eV); and MeOBC-A (740 nm, 2.14 eV) versus HBC-A (768 nm, 2.05 eV). For these pairs of compounds (with versus without the 5-methoxy group), the average bathochromic shift is 24 nm and the average shift in the HOMO-LUMO gap to lower energy is 0.09 eV. By comparison, the values for MeOBC (709 nm, 2.28 eV) versus HBC (713 nm, 2.26 eV) reveal a much smaller spectral shift of 4 nm and a corresponding smaller molecular-orbital energy-gap shift of 0.02 eV. Obviously there is interplay between the electron-donating ability of the 5-methoxy group and the sensitivity of the 3,13-positions to the presence of auxochromes such as carbonyl moieties.

(4) The DFT calculations of the benchmark compounds reproduce the finding that the 2,12-dimethyl groups of bacterio-13$^1$-oxophorbine MeOBOP, and in analogy the 2-ethyl group of MeOBC-I and HBC-I, have little effect. This result is shown by the $Q_y(0,0)$ wavelength and the HOMO-LUMO energy gap for the following pairs of compounds: HBC-A (768 nm, 2.05 eV) versus HBC-MeA (766 nm, 2.02 eV); and MeOBC-A (740 nm, 2.14 eV) versus MeOBC-MeA (743 nm, 2.14 eV). In both cases the presence of the 2,12-dimethyl groups results in ≤3 nm spectral shift and a ≤0.03 eV shift in the molecular-orbital energy gap. Collectively, these results suggest that the alkyl groups at the 2- or 12-positions of MeOBOP, MeOBC-I and HBC-I, and by implication the native photosynthetic pigments such as BPh-a, play an insignificant role in determining the spectral properties of these molecules.

(5) The data and analysis given above (Table 1 and FIGS. 1 and 2) provide insights into which substituents are most responsible for the spectral characteristics of MeOBOP versus that of the benchmark bacteriochlorin MeOBC. The $Q_y(0,0)$ position and HOMO-LUMO gap for MeOBC (709 nm, 2.28 eV) are strongly affected upon the addition of the 3,13-diacetyl groups (MeOBC-A: 740 nm, 2.14 eV), with little further effect upon addition of the 2,12-dimethyl groups (MeOBC-MeA: 743 nm, 2.14 eV). The final step to obtain MeOBOP (733 nm, 2.18 eV) is closure to form the five-membered ring. The latter can be thought of as first, placement of a substituent at the 15-methyl group, and second, ring closure accompanied by structural/electronic effects such as ring strain and shift toward planarity. To gain insights into the effect of the 15-substituent, DFT calculations were carried out on the fictive bacteriochlorin MeOBC-MeAMe[15], wherein a methyl group is placed at the 15-position (Chart 3, Tables 1 and 2). The HOMO-LUMO energy gap (2.17 eV) for this fictive compound is between those for MeOBC-MeA (2.14 eV) and MeOBOP (2.18 eV), consistent with a modest effect of substitution at the 15-position. Given the small (0.03-0.04 eV) energy shifts involved, however, the effects of 15-substitution versus ring closure (once the 13-acetyl group is in place) are of uncertain relative magnitude in dictating the ultimate spectral properties of the bacterio-13$^1$-oxophorbine chromophores.

Outlook

Bacteriochlorophylls are Nature's pigments for absorption of sunlight in the near-infrared region. The ability to utilize such compounds in diverse artificial systems—such as artificial photosynthesis, clinical diagnostics, and photomedicine—depends on versatile synthetic methods that afford stable macrocycles and that enable the spectral properties to be tuned at will. The designs we have chosen employ a geminal dimethyl group in each pyrroline ring to ensure stability toward adventitious dehydrogenation. The resulting synthetic bacteriochlorins thus differ slightly in structure from the natural pigments, yet are more robust toward routine handling and synthetic manipulation. Here we have explored the ability to install an exocyclic ring, either the five-membered "ring E" as occurs in all bacteriochlorophylls, or the six-membered imide ring characteristic of derivatives of bacteriochlorophylls commonly known as bacteriopurpurinimides.

Of the de novo synthesized bacteriochlorins that we have prepared to date, MeOBC[46] and HBC[45] are at the shorter wavelength end of the range of $Q_y(0,0)$ absorption positions while the two bacteriochlorin-imides MeOBC-I and HBC-I are at the longer extreme. A naturally occurring bacteriochlorin (wherein each pyrroline ring bears a geminal dialkyl unit and an oxo group) known as tolyporphin A absorbs at 678 nm.[68] The ability to tune the absorption band almost at will from ~680-820 nm bodes well for the use of synthetic bacteriochlorins, bacterio-13$^1$-oxophorbines, and bacteriochlorin-13,15-dicarboximides in diverse photochemical applications. The pursuit of such applications will be facilitated by the fluorescence yields (0.036-0.19), singlet excited-state lifetimes (1.9-4.6 ns), and photostability of the bacterio-13$^1$-oxophorbine and bacteriochlorin-13,15-dicarboximides prepared herein, as well as the obvious sites for synthetic elaboration provided by the keto and N-imide groups of the annulated ring E.

Experimental Section

General Methods $^1$H NMR spectra (300 MHz) and $^{13}$C NMR spectra (100 MHz) were collected at room temperature in CDCl$_3$. Silica gel (40 μm average particle size) was used for column chromatography. All solvents were reagent grade and were used as received unless noted otherwise. THF was freshly distilled from sodium/benzophenone ketyl. Laser-desorption mass spectrometry was performed without any matrix. Electrospray ionization mass spectrometry (ESI-MS) data are reported for the molecule ion or protonated molecule ion. Known compounds 3-methyl-pyrrole-2-carboxaldehyde (2),[57] 1,1-dimethoxy-4-methyl-3-penten-2-one (5),[44] and two bacteriochlorins (HBC-EtEs, MeOBC-EtEs-Br[15])[46] were prepared according to literature procedures.

3,13-Diacetyl-5-methoxy-8,8,18,18-tetramethylbacteriochlorin (MeOBC-A)

Following a procedure for replacement of a bromo group with an acetyl group on a bacteriochlorin with modification,[46,58] a mixture of MeOBC-Br (108 mg, 0.194 mmol), tributyl (1-ethoxyvinyl)tin (135 μL, 0.388 mmol), and (PPh$_3$)$_2$PdCl$_2$ (56 mg, 0.078 mmol) was heated in acetonitrile/DMF [20 mL, (3:2)] at 85° C. for 1.5 h. The reaction mixture was treated with 10% aqueous HCl (50 mL) at room temperature for 20 min and then diluted with CH$_2$Cl$_2$. The reaction mixture was poured into a saturated aqueous solution of NaHCO$_3$ and extracted with dichloromethane. The organic layer was dried (Na$_2$SO$_4$), concentrated and chromatographed (silica, CH$_2$Cl$_2$) to afford a purple solid (64 mg, 68%): $^1$H NMR δ −1.68 (brs, 1H), −1.31 (brs, 1H), 1.90 (s, 6H), 1.95 (s, 6H), 3.08 (s, 3H), 3.16 (s, 3H), 4.18 (s, 3H), 4.36 (s, 2H), 4.39 (s, 2H), 8.54 (s, 1H), 8.63 (s, 1H), 8.66 (d, J=2.2 Hz, 1H), 9.08 (d, J=1.93 Hz, 1H), 9.77 (s, 1H); $^{13}$C NMR δ 29.9, 31.0, 31.3, 33.2, 45.5, 46.1, 48.2, 51.6, 64.9, 97.6, 99.6, 99.8, 121.3, 125.7, 128.3, 129.1, 133.0, 135.1, 135.6, 135.7, 135.9, 157.2, 162.5, 169.2, 172.8, 197.0, 202.5; ESI-MS obsd 485.25401; calcd 485.25527 [(M+H)$^+$, M=C$_{29}$H$_{32}$N$_4$O$_3$]; $\lambda_{abs}$ (CH$_2$Cl$_2$) 362, 530, 742 nm.

3,13-Bis(2-methyl-1,3-dioxolan-2-yl)-5-methoxy-8,8,18,18-tetramethylbacterio-chlorin (MeOBC-K)

Following a known procedure,[56] solution of MeOBC-A (20.0 mg, 0.0413 mmol) in CH$_2$Cl$_2$ (3.5 mL) was treated with ethylene glycol (470 μL, 82.6 mmol) and TMSCl (422 μL, 3.30 mmol). The mixture was stirred at room temperature for 6 h. A saturated aqueous solution of NaHCO$_3$ was added and the mixture was extracted with CH$_2$Cl$_2$. The organic layer was separated, dried (Na$_2$SO$_4$) and concentrated under vacuum. Column chromatography (alumina, CH$_2$Cl$_2$) afforded a green solid (17 mg, 72%): NMR δ −2.06 (brs, 1H), −1.86 (brs, 1H), 1.95 (s, 6H), 1.95 (s, 6H), 2.33 (s, 3H), 2.40 (s, 3H), 4.12-4.33 (m, 4H), 4.25 (s, 3H), 4.34-4.50 (m, 4H), 4.42 (s, 2H), 4.44 (s, 2H), 8.58 (s, 1H), 8.58 (s, 1H), 8.73 (d, J=2.75 Hz, 1H), 8.79 (d, J=2.75 Hz, 1H), 9.08 (s, 1H); LD-MS obsd 572.7, calcd 572.3 (C$_{33}$H$_{40}$N$_4$O$_5$); λ$_{abs}$ (CH$_2$Cl$_2$) 356, 367, 505, 715 nm.

8-Bromo-2,3-dihydro-1-(1,1-dimethoxymethyl)-3,3,7-trimethyldipyrrin (1)

Following a procedure for the synthesis of bromo-dihydrodipyrrin-acetals,[50] in a first flask a solution of 6-H (4.77 g, 12.2 mmol) in freshly distilled THF (30 mL) at 0° C. was treated with freshly prepared NaOMe (3.3 g, 61 mmol). The resulting mixture was stirred and degassed by bubbling argon through the solution for 45 m. In a second flask purged with argon, TiCl$_3$ (46 mL, 20% in 3% HCl solution, 73 mmol), THF (90 mL), NH$_4$OAc (35 g, 0.46 mol), and degassed water (50 mL) were combined under argon and the solution was degassed by bubbling argon through the solution for 45 min. Then the first flask mixture was transferred via cannula to the buffered TiCl$_3$ solution. The resulting mixture was stirred at room temperature for 16 h under argon. A saturated solution of aqueous NaHCO$_3$ (300 mL) was added followed by ethyl acetate (200 mL). The mixture was extracted with ethyl acetate. The organic layer was dried (Na$_2$SO$_4$), concentrated to a brown oil, dried under high vacuum for 2 h, and chromatographed on a short alumina column (neutral alumina, CH$_2$Cl$_2$) to give a light brown oil (1.40 g, 34%): $^1$H NMR δ 1.22 (s, 6H), 2.10 (s, 3H), 2.62 (s, 2H), 3.44 (s, 6H), 5.01 (s, 1H), 5.80 (s, 1H), 6.73-6.84 (m, 1H), 10.66 (brs, 1H); $^{13}$C NMR δ 10.1, 29.4, 40.5, 48.4, 54.8, 99.6, 102.9, 105.1, 117.3, 117.9, 127.5, 159.9, 174.7; ESI-MS obsd 341.0865, calcd 341.0859 [(M+H)$^+$, M=C$_{15}$H$_{21}$BrN$_2$O$_2$].

4-Bromo-3-methylpyrrole-2-carboxaldehyde (3)

Following a general procedure,[50] a stirred solution of 3-methyl-pyrrole-2-carboxaldehyde (2, 5.63 g, 51.6 mmol) in THF (52 mL) was cooled to 0° C. NBS (9.19 g, 51.6 mmol; reagent grade, unrecrystallized) was added all at once. The reaction mixture was stirred for 15 min at 0° C. under argon before the solvent was removed on a rotary evaporator. The resulting solid was dried under high vacuum for 2 h. Water (100 mL, room temperature) was added to the flask and the suspension was filtered (Büchner funnel). The filter cake was washed with an additional 100 mL of water. The solid filtered material was recrystallized from water/ethanol as follows. The solid filtered material was transferred to a 250 mL round bottom flask equipped with a reflux condenser. Water/ethanol (150 mL, 5:1) were added and the mixture was refluxed in a hot water bath until all solid material had dissolved. Upon allowing the solution to cool to room temperature the product crystallized. The mixture was cooled to 4° C. for 2 h to promote more crystallization. The mixture was vacuum-filtered and the resulting off-white crystals were dried under high vacuum for 24 h (7.78 g, 80%): mp 140-143° C.; $^1$H NMR δ 2.32 (s, 3H), 7.08 (d, J=3.3 Hz, 1H), 9.60 (s, 1H), 9.95 (brs, 1H); $^{13}$C NMR δ 9.8, 101.7, 126.0, 129.3, 131.7, 177.9; ESI-MS obsd 187.9708, calcd 187.9706 [(M+H)$^+$, M=C$_6$H$_6$BrNO].

4-Bromo-3-methyl-2-formyl-N-tosylpyrrole (3-Ts)

Following a general procedure,[50] a stirred suspension of 60% NaH (2.5 g, 62 mmol) in dry THF (42 mL, distilled) was cooled to 0° C. under argon. The mixture was treated portionwise with 3 (7.78 g, 41.4 mmol). The mixture was stirred for 30 min at 0° C. before treating all at once with p-toluenesulfonyl chloride (8.00 g, 41.4 mmol). The reaction mixture was stirred at room temperature for 3 h, whereupon water (100 mL) was slowly added to quench the reaction. Ethyl acetate (100 mL) was added, and the organic layer was separated. The organic layer was washed with brine, dried (Na$_2$SO$_4$), and concentrated to a solid. The solid was dried under high vacuum for 2 h. The crude solid material was dissolved in 100 mL hexanes/ethyl acetate (5:1) by refluxing in a hot water bath. Upon allowing the solution to cool to room temperature the product crystallized. The mixture was cooled overnight at −10° C. to promote additional crystallization. The mixture was vacuum-filtered, and the resulting light brown crystals were dried under high vacuum (9.73 g, 69%): mp 152-155° C.; $^1$H NMR δ 2.29 (s, 3H), 2.43 (s, 3H), 7.34 (d, J=8.5 Hz, 2H), 7.55 (s, 1H), 7.76 (d, J=8.5 Hz, 2H), 10.14 (s, 1H); $^{13}$C NMR δ 2.1, 22.0, 106.2, 126.8, 127.6, 129.1, 130.6, 135.2, 136.4, 146.5, 180.1; Anal. Calcd for C$_{13}$H$_{12}$BrNO$_3$S: C, 45.63; H, 3.53; N, 4.09. Found: C, 45.71; H, 3.44; N, 4.11.

4-Bromo-3-methyl-2-(2-nitroethyl)-N-tosylpyrrole (4-Ts)

Following a general procedure,[50] a stirred mixture of 3-Ts (7.73 g, 28.5 mmol) in the form of a finely ground powder, potassium acetate (2.24 g, 22.8 mmol), methylamine hydrochloride (1.54 g, 22.8 mmol), and acetic acid (0.1 mL) in absolute ethanol (10 mL) was treated with nitromethane (4.0 mL, 78 mmol). The mixture was stirred for 2 h, whereupon water was added (100 mL) and the resulting yellow precipitate was filtered by vacuum filtration. The solid filtered material was washed with water (200 mL) followed by cold ethanol (~100 mL, 0° C.) until the eluant was clear. The yellow filtered solid was dried overnight under high vacuum. The crude solid material was dissolved in dry THF (117 mL, distilled). The solution was cooled to −10° C. (internal temperature, using an acetone bath with a few pieces of dry ice) under argon. The solution was treated with 95% LiBH$_4$ (0.64 g, 28 mmol) all at once under vigorous stirring. The reaction mixture was stirred for ~15 min at −10° C., until all of the starting material disappeared (starting material: CH=CHNO$_2$: d, J=13.6 Hz, 8.56 ppm; product: CH$_2$CH$_2$NO$_2$: t, J=7.3 Hz, 4.54 ppm and 3.36 ppm), whereupon the reaction mixture was quenched by slowly adding a cold saturated aqueous NH$_4$Cl solution (200 mL, 0° C.). The mixture was extracted with ethyl acetate (200 mL). The organic layer was washed with brine, dried (Na$_2$SO$_4$), and concentrated to a solid. The solid was dried under high vacuum for 2 h. The crude solid material was dissolved in 100 mL of 2-propanol by refluxing in a hot water bath. Upon cooling the solution to −10° C. the product crystallized. The mixture was vacuum-filtered, and the resulting light brown crystals were dried under high vacuum (9.03 g, 82%): mp 85° C.; $^1$H NMR δ 1.92 (s, 3H), 2.43 (s, 3H), 3.36 (t, J=7.3 Hz, 2H), 4.54 (t, J=7.3 Hz, 2H), 7.34 (d, J=8.4 Hz, 2H), 7.34 (s, 1H), 7.66 (d, J=8.4 Hz, 2H); $^{13}$C NMR δ 10.5, 21.9, 24.3, 74.3, 105.2, 121.7, 124.3, 124.9, 126.9, 130.6, 135.6, 146.0; ESI-MS obsd 387.0024, calcd 387.0009 [(M+H)$^+$, M=C$_{14}$H$_{15}$BrN$_2$O$_4$S];

6-(4-Bromo-3-methyl-N-tosylpyrrol-2-yl)-1,1-dimethoxy-4,4-dimethyl-5-nitrohexan-2-one (6-Ts)

Following a general procedure,[50] a mixture of 4-Ts (9.00 g, 23.3 mmol) and 1,1-dimethoxy-4-methyl-3-penten-2-one (11.1 g, 69.9 mmol, 3 equiv) was treated with DBU (10.5 mL, 69.9 mmol). The reaction mixture was stirred for 15 min under argon. A saturated solution of cold aqueous NH$_4$Cl (50 mL, 0° C.) was added. The mixture was extracted with ethyl acetate (100 mL). The organic layer was washed with brine, dried (Na$_2$SO$_4$), concentrated and dried overnight under high vacuum. Addition of diethyl ether (50 mL) to the resulting solid, trituration, and filtration afforded a pale brown solid (11.0 g, 86%): mp 114-115° C.; $^1$H-NMR δ 1.22 (s, 3H), 1.27 (s, 3H), 1.85 (s, 3H), 2.42 (s, 3H), 2.64, 2.74 (AB, $^2$J=19.0 Hz, 2H), 3.15 (ABX, $^2$J$_{AB}$=15.4 Hz, $^3$J$_{BX}$=1.8 Hz, 1H), 3.32 (ABX, $^2$J$_{AB}$=15.4 Hz, $^3$J$_{AX}$=11.7 Hz, 1H), 3.41 (s, 3H), 3.43 (s, 3H), 4.37 (s, 1H), 5.19 (ABX, $^3$J$_{AX}$=11.7 Hz, $^3$J$_{BX}$=1.8 Hz, 1H), 7.28 (s, 1H), 7.31 (d, J=8.1 Hz, 2H), 7.59 (d, J=8.1 Hz, 2H); $^{13}$C NMR δ 0.7, 21.9, 23.8, 24.0, 25.9, 36.8, 44.2, 55.28, 55.29, 94.4, 104.9, 105.9, 122.6, 125.1, 125.9, 126.7, 130.5, 135.9, 145.6, 203.2; Anal. Calcd for C$_{22}$H$_{29}$BrN$_2$O$_7$S: C, 48.44; H, 5.36; N, 5.14. Found: C, 48.70; H, 5.30; N, 5.17.

6-(4-Bromo-3-methyl-1H-pyrrol-2-yl)-1,1-dimethoxy-4,4-dimethyl-5-nitrohexan-2-one (6-H)

Following a general procedure,[50] a sample of 6-Ts (9.12 g, 16.7 mmol) was treated with TBAF (34 mL, 1.0 M in THF, 34 mmol), and the reaction mixture was stirred for 1 h at reflux. A saturated solution of aqueous NaHCO$_3$ (100 mL) was added followed by ethyl acetate (50 mL). The mixture was extracted with ethyl acetate. The organic layer was dried (Na$_2$SO$_4$), concentrated to a brown oil, dried under high vacuum for 2 h, and chromatographed (silica, CH$_2$Cl$_2$) to give a light brown oil (4.00 g, 61%): $^1$H NMR δ 1.13 (s, 3H), 1.22 (s, 3H), 1.95 (s, 3H), 2.60, 2.70 (AB, $^2$J=18.8 Hz, 2H), 2.99 (ABX, $^2$J$_{AB}$=15.4 Hz, $^3$J$_{BX}$=2.5 Hz, 1H), 3.24 (ABX, $^2$J$_{AB}$=15.4 Hz, $^3$J$_{AX}$=11.8 Hz, 1H), 3.41 (s, 3H), 3.42 (s, 3H), 4.38 (s, 1H), 5.12 (ABX, $^3$J$_{AX}$=11.8 Hz, $^3$J$_{BX}$=2.5 Hz, 1H), 6.59 (s, 1H), 8.29 (brs, 1H); $^{13}$C NMR δ 9.8, 24.4, 24.4, 25.6, 36.6, 45.4, 55.39, 55.40, 94.1, 99.0, 104.7, 116.1, 116.7, 122.5, 204.2; ESI-MS obsd 391.0864, calcd 391.0863 [(M+H)$^+$, M=C$_{15}$H$_{23}$BrN$_2$O$_5$].

3,13-Dibromo-5-methoxy-2,8,8,12,18,18-hexamethylbacteriochlorin (MeOBC-MeBr)

Following a general procedure,[46] a solution of 1 (675 mg, 1.98 mmol, 18 mM) in anhydrous CH$_2$Cl$_2$ (110 mL) was treated first with 2,6-DTBP (3.61 mL, 15.8 mmol, 144 mM) and second with TMSOTf (1.44 mL, 7.92 mmol, 72 mM). The reaction mixture was stirred at room temperature for 16 h. The reaction mixture was concentrated, and the residue was chromatographed [silica, hexanes/CH$_2$Cl$_2$ (1:1)]. A single green band was collected and concentrated to a green solid (122 mg, 21%): $^1$H NMR δ −1.99 (brs, 1H), −1.78 (brs, 1H), 1.94 (s, 6H), 1.96 (s, 6H), 3.38 (s, 3H), 3.41 (s, 3H), 4.32 (s, 3H), 4.40 (s, 2H), 4.43 (s, 2H), 8.53 (s, 1H), 8.57 (s, 1H), 8.72 (s, 1H); $^{13}$C NMR δ 13.0, 13.2, 31.2, 31.4, 45.9, 46.1, 47.6, 52.0, 64.5, 94.1, 94.4, 95.8, 106.8, 113.0, 125.7, 129.9, 131.8, 132.4, 133.8, 134.9, 160.9; ESI-MS obsd 585.0837, calcd 585.0859 [(M+H)$^+$, M=C$_{27}$H$_{30}$Br$_2$N$_4$O]; λ$_{abs}$ (CH$_2$Cl$_2$) 351, 373, 502, 725 nm.

3,13-Dibromo-2,8,8,12,18,18-hexamethylbacteriochlorin (HBC-MeBr)

Following a general procedure,[44,46] a solution of 1 (1.36 g, 3.99 mmol, 5 mM) in anhydrous CH$_3$CN (800 mL) was treated with BF$_3$.OEt$_2$ (4.9 mL, 40 mmol, 50 mM). The reaction mixture was stirred at room temperature for 16 h. Excess TEA (6.0 mL) was added to the reaction mixture. The reaction mixture was concentrated, and the residue was chromatographed [silica, hexanes/CH$_2$Cl$_2$ (1:1)] to afford a green solid (139 mg, 13%): $^1$H NMR δ −2.15 (brs, 2H), 1.96 (s, 12H), 3.40 (s, 6H), 4.46 (s, 4H), 8.60 (s, 2H), 8.87 (s, 2H); ESI-MS obsd 555.0745, calcd 555.0753 [(M+H)$^+$, M=C$_{26}$H$_{28}$Br$_2$N$_4$]; λ$_{abs}$ (CH$_2$Cl$_2$) 346, 371, 491, 731 nm.

3,13-Diacetyl-5-methoxy-2,8,8,12,18,18-hexamethylbacteriochlorin (MeOBC-MeA)

Following a procedure for replacement of a bromo group with an acetyl group on a bacteriochlorin,[45,58] a mixture of MeOBC-MeBr (82 mg, 0.14 mmol), tributyl(1-ethoxyvinyl)tin (195 µL, 0.56 mmol) and (PPh$_3$)$_2$PdCl$_2$ (98 mg, 0.14 mmol) was refluxed in THF (14 mL) for 23 h in a Schlenk flask. The reaction mixture was treated with 10% aqueous HCl (40 mL) at room temperature for 10 min. The reaction mixture was poured into a saturated aqueous solution of NaHCO$_3$ and extracted with dichloromethane. The organic layer was dried (Na$_2$SO$_4$), concentrated and chromatographed [silica, CH$_2$Cl$_2$/EtOAc (99:1)] to give a purple solid (23 mg, 32%): $^1$H NMR δ −1.84 (brs, 1H), −1.55 (brs, 1H), 1.93 (s, 6H), 1.97 (s, 6H), 2.98 (s, 3H), 3.20 (s, 3H), 3.33 (s, 3H), 3.62 (s, 3H), 4.15 (s, 3H), 4.35 (s, 2H), 4.39 (s, 2H), 8.50 (s, 1H), 8.64 (s, 1H), 9.35 (s, 1H); ESI-MS obsd 513.2857, calcd 513,2860 [(M+H)$^+$, M=C$_{31}$H$_{36}$N$_4$O$_3$]; λ$_{abs}$ (CH$_2$Cl$_2$) 362, 523, 743 min.

3,13-Diacetyl-2,8,8,12,18,18-hexamethylbacteriochlorin (HBC-MeA)

Following a procedure for replacement of a bromo group with an acetyl group on a bacteriochlorin,[45,58] a mixture of HBC-MeBr (40 mg, 0.072 mmol), tributyl(1-ethoxyvinyl)tin (100 µL, 0.288 mmol) and (PPh$_3$)$_2$PdCl$_2$ (51 mg, 0.072 mmol) was refluxed in THF (7 mL) for 23 h in a Schlenk flask. The reaction mixture was treated with 10% aqueous HCl (40 mL) at room temperature for 10 min. The reaction mixture was poured into a saturated aqueous solution of NaHCO$_3$ and extracted with dichloromethane. The organic layer was dried (Na$_2$SO$_4$), concentrated and chromatographed (silica, CH$_2$Cl$_2$) to give a purple solid (12 mg, 35%): $^1$H NMR δ −1.32 (brs, 2H), 1.94 (s, 12H), 3.19 (s, 6H), 3.61 (s, 6H), 4.39 (s, 4H), 8.59 (s, 2H), 9.35 (s, 2H); ESI-MS obsd 483.2755, calcd 483.2755 [(M+H)$^+$, M=C$_{30}$H$_{34}$N$_4$O$_2$]; λ$_{abs}$ (CH$_2$Cl$_2$) 359, 389, 523, 766 nm.

3,13-Diacetyl-15-bromo-5-methoxy-2,8,8,12,18,18-hexamethylbacteriochlorin (MeOBC-MeA-Br$^{15}$)

A solution of MeOBC-MeA (8.0 mg, 0.015 mmol) in THF (6.5 mL) was treated with NBS (2.9 mg, 0.015 mmol, from 0.50 M freshly prepared THF stock solution) at room temperature for 1 h. TLC analysis (silica, CH$_2$Cl$_2$) showed the disappearance of starting material and the presence of only one new spot. The reaction mixture was diluted with $CH_2Cl_2$ and washed with saturated aqueous $NaHCO_3$. The organic layer was dried ($Na_2SO_4$), concentrated and chromatographed (silica, $CH_2Cl_2$) to afford a green solid (6.2 mg, 70%): $^1$H NMR δ −2.09 (brs, 1H), −1.87 (brs, 1H), 1.94 (s, 6H), 1.95 (s, 6H), 2.99 (s, 3H), 3.03 (s, 3H), 3.31 (s, 3H), 3.34 (s, 3H), 4.15 (s, 3H), 4.35 (s, 2H), 4.41 (s, 2H), 8.51 (s, 1H), 8.58 (s, 1H); ESI-MS obsd 512.2782, calcd 512.2782 [(M−Br+H)$^+$, M=$C_{31}H_{35}BrN_4O_3$]; $\lambda_{abs}$ ($CH_2Cl_2$) 365, 376, 517, 726 nm.

3,13-Diacetyl-5,15-dibromo-2,8,8,12,18,18-hexamethylbacteriochlorin (BC-MeA-Br$^{5,15}$)

A solution of HBC-MeA (17 mg, 0.035 mmol) in THF (18 mL) was treated with NBS (6.3 mg, 0.035 mmol, from 0.50 M freshly prepared THF stock solution) at room temperature for 1 h. TLC analysis (silica, $CH_2Cl_2$) showed unreacted starting material and a new component. The reaction mixture was diluted with $CH_2Cl_2$ and washed with saturated aqueous $NaHCO_3$. The organic layer was dried ($Na_2SO_4$), concentrated and chromatographed (silica, $CH_2Cl_2$). The first band (purple) was remaining starting bacteriochlorin (4.0 mg) and the second band (green) was the (dibrominated) title compound (5.0 mg, 22%): $^1$H NMR δ −1.77 (brs, 2H), 1.94 (s, 12H), 3.04 (s, 6H), 3.32 (s, 6H), 4.42 (s, 4H), 8.56 (s, 2H); ESI-MS obsd 638.0887 and 559.1700, calcd 638.0892 and 559.1709 [(M)$^+$ and (M−Br)$^+$, M=$C_{30}H_{32}Br_2N_4O_2$]; $\lambda_{abs}$ ($CH_2Cl_2$) 359, 381, 518, 732 nm.

3-Acetyl-5-methoxy-2,8,8,12,18,18-hexamethylbacterio-13$^1$-oxophorbine (MeOBOP)

Following a reported procedure,$^{53}$ a mixture of MeOBC-MeA-Br$^{15}$ (9.0 mg, 0.015 mmol), $Cs_2CO_3$ (25 mg, 0.077 mmol), and (PPh$_3$)$_2$PdCl$_2$ (11 mg, 0.015 mmol) was refluxed in toluene (1.6 mL) for 20 h in a Schlenk flask. The reaction mixture was cooled to room temperature and chromatographed [silica, $CH_2Cl_2$/THF (99:1)] to afford a purple solid (6.6 mg, 86%): NMR δ −1.39 (brs, 1H), 0.12 (brs, 1H), 1.90 (s, 6H), 1.91 (s, 6H), 2.91 (s, 3H), 3.23 (s, 3H), 3.46 (s, 3H), 4.05 (s, 2H), 4.07 (s, 3H), 4.27 (s, 2H), 4.88 (s, 2H), 8.25 (s, 1H), 8.39 (s, 1H); ESI-MS obsd 511.2701, calcd 511.2704 [(M+H)$^+$, M=$C_{31}H_{34}N_4O_3$]; IR (NaCl) v, cm$^{-1}$ 3435, 2954, 2918, 2850, 1687, 1630, 1360, 1226, 1132, 1084; $\lambda_{abs}$ (toluene) 359, 372, 530, 733 nm.

15$^2$-N-Benzyl-3-ethoxycarbonyl-2,12-diethyl-5-methoxy-8,8,18,18-tetramethyl-bacteriochlorin-13,15-dicarboximide (MeOBC-I)

Following a reported procedure,$^{54}$ a mixture of MeOBC-EtEs-Br$^{15}$ (7.7 mg, 0.011 mmol), Pd(PPh$_3$)$_4$ (13 mg, 0.011 mmol), and $Cs_2CO_3$ (11 mg, 0.034 mmol) were dried under high vacuum in a Schlenk flask for 1 h. The flask was then filled with CO and THF (1.5 mL) containing benzylamine (5 μL, 0.05 mmol) was added. The reaction mixture was then stirred at 80° C. for 20 h under a CO atmosphere. The reaction mixture was cooled to room temperature and chromatographed (silica, $CH_2Cl_2$) to afford a purple solid (4.8 mg, 62%): $^1$H NMR δ −0.90 (brs, 1H), −0.43 (brs, 1H), 1.61 (t, J=7.2 Hz, 3H), 1.73 (m, 6H), 1.87 (s, 6H), 1.90 (s, 6H), 3.73 (q, J=7.7 Hz, 2H), 4.15-4.28 (q, J=7.2 Hz, 2H), 4.22 (s, 3H), 4.25 (s, 2H), 4.69 (s, 2H), 4.75 (q, J=7.2 Hz, 2H), 5.67 (s, 2H), 7.32-7.44 (m, 3H), 7.74 (d, J=7.4 Hz, 2H), 8.40 (s, 1H), 8.68 (s, 1H); ESI-MS obsd 688.3496, calcd 688.3493 [(M+H)$^+$, M=$C_{41}H_{45}N_5O_5$]; IR (NaCl) v, cm$^{-1}$ 3435, 3386, 2959, 2919, 1728, 1682, 1647, 1537, 1215, 1149, 1126, 1088; $\lambda_{abs}$ (toluene) 351, 371, 407, 550, 793 nm.

15-Bromo-3,13-diethoxycarbonyl-2,12-diethyl-8,8,18,18-tetramethylbacteriochlorin (HBC-EtEs-Br$^{15}$)

A solution of HBC-EtEs (50 mg, 0.088 mmol) in THF (35 mL) was treated with NBS (16 mg, 0.088 mmol, from 0.50 M freshly prepared THF stock solution) at room temperature for 1 h. The reaction mixture was diluted with $CH_2Cl_2$ and washed with saturated aqueous $NaHCO_3$. The organic layer was dried ($Na_2SO_4$), concentrated and chromatographed (silica, $CH_2Cl_2$) to afford a green solid (10. mg, 18%): NMR δ −1.61 (brs, 1H), −1.50 (brs, 1H), 1.60 (t, J=7.2 Hz, 6H), 1.66-1.84 (m, 6H), 1.94 (s, 6H), 1.95 (s, 6H), 3.82 (q, J=7.7 Hz, 2H), 4.15 (q, J=7.4 Hz, 2H), 4.41 (s, 2H), 4.43 (s, 2H), 4.77 (m, 4H), 8.58 (s, 1H), 8.64 (s, 1H), 9.63 (s, 1H); ESI-MS obsd 649.2383, calcd 649.2384 [(M+H)$^+$, M=$C_{34}H_{41}BrN_4O_4$]; $\lambda_{abs}$ ($CH_2Cl_2$) 354, 380, 520, 748 nm.

15$^2$-N-Benzyl-3-ethoxycarbonyl-2,12-diethyl-8,8,18,18-tetramethylbacteriochlorin-13,15-dicarboximide (HBC-I)

Following a reported procedure,$^{54}$ a mixture of HBC-EtEs-Br$^{15}$ (9.7 mg, 0.011 mmol), Pd(PPh$_3$)$_4$ (17 mg, 0.015 mmol), and $Cs_2CO_3$ (15 mg, 0.045 mmol) were dried under high vacuum in a Schlenk flask. The flask was then filled with CO and THF (2.0 mL) containing benzylamine (7 μL, 0.06 mmol) was added. The reaction mixture was then stirred at 80° C. for 20 h under a CO atmosphere. The reaction mixture was cooled to room temperature and chromatographed (silica, $CH_2Cl_2$) to afford a purple solid (4.0 mg, 44%): $^1$H NMR δ −0.69 (brs, 1H), −0.47 (brs, 1H), 1.71 (m, 9H), 1.90 (s, 6H), 1.92 (s, 6H), 3.99-4.15 (q, J=7.2 Hz, 2H), 4.16-4.29 (q, J=7.4 Hz, 2H), 4.33 (s, 2H), 4.72 (s, 2H), 4.77 (q, J=7.2 Hz, 2H), 5.68 (s, 2H), 7.31-7.44 (m, 3H), 7.70-7.82 (m, 2H), 8.56 (s, 1H), 8.71 (s, 1H), 9.54 (s, 1H); ESI-MS obsd 658.3399, calcd 658.3388 [(M+H)$^+$, M=$C_{40}H_{43}N_5O_4$]; IR (NaCl) v, cm$^{-1}$ 3431, 2956, 2918, 2848, 1680, 1649, 1423, 1217, 1149, 1095; $\lambda_{abs}$ (toluene) 359, 408, 544, 818 nm.

Photophysical Measurements.

Static absorption and fluorescence measurements were performed as described previously.$^{69,70}$ Argon-purged solutions of the samples in toluene with an absorbance of ≤0.10 at the excitation wavelength were used for the fluorescence spectral, quantum yield, and lifetime measurements. Fluorescence lifetimes were obtained using a phase modulation technique and Soret-band excitation$^{70}$ or via decay measurements using Soret-region excitation pulses obtained from a nitrogen-pumped dye laser and time-correlated-single-photon-counting detection. Emission measurements employed 2-4 nm excitation- and detection-monochromator bandwidths and 0.2 nm data intervals. Emission spectra were corrected for detection-system spectral response. Fluorescence quantum yields were determined relative to free base tetraphenylporphyrin ($\Phi_f$=0.090),$^{71}$ chlorophyll a in benzene ($\Phi_f$=0.325)$^{72}$ or chlorophyll a in toluene (which was found here to have the same value as in benzene).

Density Functional Theory Calculations.

DFT calculations were performed with Spartan '08 for Windows version 1.2.0 in parallel mode$^{73}$ on a PC equipped with an Intel i7-975 cpu, 24 GB ram, and three 300 GB, 10 k rpm hard drives. The hybrid B3LYP functional and the 6-31G* set were employed. The equilibrium geometries were fully optimized using the default parameters of the Spartan '08 program.

REFERENCES (1) M. Kobayashi, M. Akiyama, H. Kano and H. Kise, in *Chlorophylls and Bacteriochlorophylls: Biochemistry, Biophysics, Functions and Applications*, ed. B. Grimm, R. J. Porra, W. Rüdiger and H. Scheer, Springer, Dordrecht, The Netherlands, 2006, vol. 25, ch. 6, pp. 79-94.
(2) M. Wasielewski and W. A. Svec, *J. Org. Chem.*, 1980, 45, 1969-1974.
(3) A. Osuka, S. Marumo, Y. Wada, I. Yamazaki, T. Yamazaki, Y. Shirakawa and Y. Nishimura, *Bull. Chem. Soc. Jpn.*, 1995, 68, 2909-2915.
(4) T. Miyatake, H. Tamiaki, A. R. Holzwarth and K. Schaffner, *Photochem. Photobiol.*, 1999, 69, 448-456.
(5) H. Mossier, M. Wittenberg, D. Niethammer, R. K. Mudrassagam, H. Kurreck and M. Huber, *Mag. Reson. Chem.*, 2000, 38, 67-84.
(6) M. A. Grin, I. S. Lonin, S. V. Fedyunin, A. G. Tsiprovskiy, A. A. Strizhakov, A. A. Tsygankov, A. A. Krasnovsky and A. F. Mironov, *Mendeleev Commun.*, 2007, 17, 209-211.
(7) C. Muthiah, M. Taniguchi, H.-J. Kim, I. Schmidt, H. L. Kee, D. Holten, D. F. Bocian and J. S. Lindsey, *Photochem. Photobiol.*, 2007, 83, 1513-1528,
(8) J. R. Stromberg, A. Marton, H. L. Kee, C. Kirmaier, J. R. Diers, C. Muthiah, M. Taniguchi, J. S. Lindsey, D. F. Bocian, G. J. Meyer and D. Holten, *J. Phys. Chem. C*, 2007, 111, 15464-15478.
(9) C. Muthiah, H. L. Kee, J. R. Diers, D. Fan, M. Ptaszek, D. F. Bocian, D. Holten and J. S. Lindsey, *Photochem. Photobiol.*, 2008, 84, 786-801.
(10) J. J. Schuitmaker, J. A. van Best, J. L. van Delft, T. M. A. R. Dubbelman, J. A. Oosterhuis and D. de Wolff-Rouendaal, *Invest. Ophthalmol. Vis. Sci.*, 1990, 31, 1444-1450.
(11) J. P. Rovers, M. L. de Jode, H. Rezzoug and M. F. Grahn, *Photochem. Photobiol.*, 2000, 72, 358-364.
(12) Y. Chen, A. Graham, W. Potter, J. Morgan, L. Vaughan, D. A. Bellnier, B. W. Henderson, A. Oseroff, T. J. Dougherty and R. K. Pandey, *J. Med. Chem.*, 2002, 45, 255-258.
(13) Y. Chen, G. Li and R. K. Pandey, *Curr. Org. Chem.*, 2004, 8, 1105-1134.
(14) F. H. van Duijnhoven, J. P. Rovers, K. Engelmann, Z. Krajina, S. F. Purkiss, F. A. Zoetmulder, T. J. Vogl and O. T. Terpstra, *Ann. Surg. Oncol.*, 2005,12, 808-816.
(15) A. S. Brandis, Y. Salomon and A. Scherz, in *Chlorophylls and Bacteriochlorophylls: Biochemistry, Biophysics, Functions and Applications*, ed. B. Grimm, R. J. Porra, W. Rüdiger and H. Scheer, Springer, Dordrecht, The Netherlands, 2006, vol. 25, ch. 33, pp. 485-494.
(16) A. L. Gryshuk, Y. Chen, W. Potter, T. Ohulchansky, A. Oseroff and R. K. Pandey, *J. Med. Chem.*, 2006, 49, 1874-1881.
(17) S. Fukuzumi, K. Ohkubo, X. Zheng, Y. Chen, R. K. Pandey, R. Zhan and K. M. Kadish, *J. Phys. Chem. B*, 2008, 112, 2738-2746.
(18) M. A. Grin, A. F. Mironov and A. A. Shtil, *Anti-Cancer Agents Med. Chem.*, 2008, 8, 683-697.
(19) M. M. Pereira, C. J. P. Monteiro, A. V. C. Somões, S. M. A. Pinto, L. G. Arnaut, G. F. F. Sá, E. F. F. Silva, L. B. Rocha, S. Simões and S. J. Formosinho, *J. Porphyrins Phthalocyanines*, 2009, 13, 567-573.
(20) E. F. F. Silva, C. Serpa, J. M. Dabrowski, C. J. P. Monteiro, S. J. Formosinho, G. Stochel, K. Urbanska, S. Simões, M. M. Pereira and L. G. Arnaut, *Chem. Eur. 1*, 2010, 16, 9273-9286.
(21) P. Mroz, Y.-Y. Huang, A. Szokalska, T. Zhiyentayev, S. Janjua, A.-P. Nifli, M. E. Sherwood, C.; Ruzié, K. E. Borbas, D. Fan, M. Krayer, T. Balasubramanian, E. Yang, H. L. Kee, C. Kirmaier, J. R. Diers, D. F. Bocian, D. Holten, J. S. Lindsey and M. R. Hamblin, *FASEB J.*, 2010, 24, 3160-3170.
(22) Y.-Y. Huang, P. Mroz, T. Zhiyentayev, T. Balasubramanian, C. Ruzié, M. Krayer, D. Fan, K. E. Borbas, E. Yang, H. L. Kee, C. Kirmaier, J. R. Diers, D. F. Bocian, D. Holten, J. S. Lindsey and M. R. Hamblin, *J. Med. Chem.*, 2010, 53, 4018-4027.
(23) L. Huang, Y.-Y. Huang, P. Mroz, G. P. Tegos, T. Zhiyentayev, S. K. Sharma, Z. Lu, T. Balasubramanian, M. Krayer, C. Ruzié, E. Yang, H. L. Kee, C. Kirmaier, J. R. Diers, D. F. Bocian, D. Holten, J. S. Lindsey and M. R. Hamblin, *Antimicrob. Agents Chemother.*, 2010, 54, 3834-3841.
(24) J. M. Sutton, O. J. Clarke, N. Fernandez and R. W. Boyle, *Bioconjugate Chem.*, 2002, 13, 249-263.
(25) H. L. Kee, R. Nothdurft, C. Muthiah, J. R. Diers, D. Fan, M. Ptaszek, D. F. Bocian, J. S. Lindsey, J. P. Culver and D. Holten, *Photochem. Photobiol.*, 2008, 84, 1061-1072.
(26) H. L. Kee, J. R. Diers, M. Ptaszek, C. Muthiah, D. Fan, J. S. Lindsey, D. F. Bocian and D. Holten, *Photochem. Photobiol.*, 2009, 85, 909-920.
(27) (a) S. C. De Rosa, J. M. Brenchley and M. Roederer, *Nature Med.*, 2003, 9, 112-117. (b) S. P. Perfetto, P. K. Chattopadhyay and M. Roederer, *Nature Rev. Immunol.*, 2004, 4, 648-655. (c) P. K. Chattopadhyay, D. A. Price, T. F. Harper, M. R. Betts, J. Yu, E. Gostick, S. P. Perfetto, P. Goepfert, R. A. Koup, S. C. De Rosa, M. P. Bruchez and M. Roederer, *Nature Med.*, 2006, 12, 972-977.
(28) Scheer, H. in *Chlorophylls and Bacteriochlorophylls: Biochemistry, Biophysics, Functions and Applications*, ed. B. Grimm, R. J. Porra, W. Rüdiger and H. Scheer, Springer, Dordrecht, The Netherlands, 2006, vol. 25, ch. 1, pp. 1-26.
(29) H. Tamiaki, M. Kouraba, K. Takeda, S.-I. Kondo and R. Tanikaga, *Tetrahedron:Asymm.*, 1998, 9, 2101-2111.
(30) S.-I. Sasaki and H. I Tamiaki, *Org. Chem.*, 2006, 71, 2648-2654.
(31) A. N. Kozyrev, G. Zheng, C. Zhu, T. J. Dougherty, K. M. Smith and R. K. Pandey, *Tetrahedron Lett.*, 1996, 37, 6431-6434.
(32) A. F. Mironov, M. A. Grin and A. G. Tsyprovskiy, *J. Porphyrins Phthalocyanines*, 2002, 6, 358-361.
(33) A. F. Mironov, M. A. Grin, A. G. Tsiprovskiy, V. V. Kachala, T. A. Karmakova, A. D. Plyutinskaya and R. I. Yakubovskaya, *J. Porphyrins Phthalocyanines*, 2003, 7, 725-730.
(34) A. F. Mironov, M. A. Grin, A. G. Tsiprovskii, A. V. Segenevich, D. V. Dzardanov, K. V. Golovin, A. A. Tsygnkov and Y. K. Shim, *Russ. J. Bioorg. Chem.*, 2003, 29, 190-197.
(35) A. F. Mironov, M. A. Grin, A. G. Tsiprovskii, R. A. Titeev, E. A. Nizhnik and I. S. Lonin, *Mendeleev Commun.*, 2004, 14, 204-207.
(36) A. N. Kozyrev, Y. Chen, L. N. Goswami, W. A. Tabaczynski and R. K. Pandey, *J. Org. Chem.*, 2006, 71, 1949-1960.
(37) L. N. Goswami, Y. Chen, J. Missert, G. Li, A. Pallenberg and R. K. Pandey, *Heterocycles*, 2007, 71, 1929-1949.
(38) M. A. Grin, I. S. Lonin, A. A. Lakhina, E. S. Ol'shanskaya, A. I. Makaraov, Y. L. Sebyakin, L. Y. Guryeva, P. V. Toukach, A. S. Kononikhin, V. A. Kuzmin and A. F. Mironov, *J. Porphyrins Phthalocyanines*, 2009, 13, 336-345
(39) S. Fox and R. W. Boyle, *Tetrahedron*, 2006, 62, 10039-10054.

(40) (a) T. D. Lash, *J. Porphyrins Phthalocyanines,* 2001, 5, 267-288. (b) B. E. Smith and T. D. Lash, *Tetrahedron,* 2010, 66, 4413-4422.

(41) Y. Vakrat-Haglili, L. Weiner, V. Brumfeld, A. Brandis, Y. Salomon, B. McIlroy, B. C. Wilson, A. Pawlak, M. Rozanowska, T. Sarna and A. Scherz, *J. Am. Chem. Soc.,* 2005, 127, 6487-6497.

(42) L. Limantara, P. Koehler, B. Wilhelm, R. J. Porra and H. Scheer, *Photochem. Photobiol.,* 2006, 82, 770-780.

(43) M. Galezowski and D. T. Gryko, *Curr. Org. Chem.,* 2007, 11, 1310-1338.

(44) H.-J. Kim and J. S. Lindsey, *J. Org. Chem.,* 2005, 70, 5475-5486.

(45) M. Taniguchi, D. L. Cramer, A. D. Bhise, H. L. Kee, D. F. Bocian, D. Holten and J. S. Lindsey, *New J. Chem.,* 2008, 32, 947-958.

(46) M. Krayer, M. Ptaszek, H.-J. Kim, K. R. Meneely, D. Fan, K. Secor and J. S. Lindsey, *J. Org. Chem.,* 2010, 75, 1016-1039.

(47) D. Fan, M. Taniguchi and J. S. Lindsey, *J. Org. Chem.,* 2007, 72, 5350-5357.

(48) K. E. Borbas, C. Ruzié and J. S. Lindsey, *Org. Lett.,* 2008, 10, 1931-1934.

(49) C. Ruzié, M. Krayer, T. Balasubramanian and J. S. Lindsey, *J. Org. Chem.,* 2008, 73, 5806-5820.

(50) M. Krayer, T. Balasubramanian, C. Ruzié, M. Ptaszek, D. L. Cramer, M. Taniguchi and J. S. Lindsey, *J. Porphyrins Phthalocyanines,* 2009, 13, 1098-1110.

(51) C. Ruzié, M. Krayer and J. S. Lindsey, *Org. Lett.,* 2009, 11, 1761-1764.

(52) Nomenclature of bacteriochlorin macrocycles is not fully settled.[a] We here introduce the terminology bacterio-$13^1$-oxophorbine for the annulated bacteriochlorin by analogy with the accepted nomenclature for the corresponding $13^1$-oxophorbine skeleton of chlorophylls. (a) G. P. Moss, *Pure Appl. Chem.,* 1987, 59, 779-832.

(53) J. K. Laha, C. Muthiah, M. Taniguchi and J. S. Lindsey, *J. Org. Chem.,* 2006, 71, 7049-7052.

(54) M. Ptaszek, D. Lahaye, M. Krayer, C. Muthiah and J. S. Lindsey, *J. Org. Chem.,* 2010, 75, 1659-1673.

(55) (a) H. Muratake and M. Natsume, *Tetrahedron Lett.,* 1997, 38, 7581-7582. (b) H. Muratake, M. Natsume and H. Nakai, *Tetrahedron,* 2004, 60, 11783-11803.

(56) R. K. Pandey, N. Jagerovic, J. M. Ryan, T. J. Dougherty and K. M. Smith, *Tetrahedron,* 1996, 52, 5349.

(57) (a) F. Bellamy, P. Martz and J. Streith, *Heterocycles,* 1975, 3, 395-400. (b) F. Bellamy and J. Streith, *J. Chem. Res.-S.,* 1979, 18-19.

(58) M. Kosugi, T. Sumiya, Y. Obara, M. Suzuki, H. Sano and T. Migita, *Bull. Chem., Soc. Jpn.,* 1987, 60, 767-768.

(59) a Mass, M. Taniguchi, M. Ptaszek, J. W. Springer, K. M. Faries, J. R. Diers, D. F. Bocian, D. Holten and J. S. Lindsey, *New J. Chem.,* 2011, 35, DOI: 10.1039/c0nj00652a.

(60) J. Helaja, A. Y. Tauber, Y. Abel, N. V. Tkachenko, H. Lemmetyinen, I. Kilpeläinen and P. H. Hynninen, *J. Chem. Soc., Perkin Trans.* 1, 1999, 2403-2408.

(61) M. Kunieda and H. Tamiaki, *J. Org. Chem.,* 2005, 70, 820-828.

(62) (a) H. Tamiaki, M. Amakawa, Y. Shimono, R. Tanikaga, A. R. Holzwarth and K. Schaffner, *Photochem. Photobiol.,* 1996, 63, 92-99. (b) H. Tamiaki, S. Yagai and T. Miyatake, *Bioorg. Med, Chem.,* 1998, 6, 2171-2178. (c) H. Tamiaki, M. Amakawa, A. R. Holzwarth and K. Schaffner, *Photosynth. Res.,* 2002, 71, 59-67. (d) H. Morishita and H. Tamiaki, *Tetrahedron,* 2005, 61, 6097-6107. (e) H. Tamiaki, H. Kitamoto, T. Watanabea and R. Shibata, *Photochem. Photobiol.,* 2005, 81, 170-176. (f) R. Shibata, T. Mizoguchi, T. Inazu and H. Tamiaki, *Photochem. Photobiol. Sci.,* 2007, 6, 749-757. (g) S. Sasaki, K. Mizutani, M. Kunieda and H. Tamiaki, *Tetrahedron Lett.,* 2008, 49, 4113-4115. (h) H. Morishita and H. Tamiaki, *Spectrochim. Acta A,* 2009, 72, 274-279.

(63) M. Kunieda and H. Tamiaki, *Eur. J. Org. Chem.,* 2006, 2352-2361,

(64) J. H. C. Smith and A. Benitez, in *Modern Methods of Plant Analysis*, ed. K. Paech and M. V. Tracey, Springer-Verlag, Berlin, 1955, vol. IV, pp. 142-196.

(65) D. Holten, M. Gouterman, W. W. Parson, M. W. Windsor and M. G. Rockley, *Photochem. Photobiol.,* 1976, 23, 415-423.

(66) M. Gouterman, in *The Porphyrins*, ed. D. Dolphin, Academic Press, New York, 1978, vol. 3, pp. 1-165.

(67) M. Gouterman, *J. Mol. Spectroscopy,* 1961, 6, 138-163.

(68) W. Wang and Y. Kishi, *Org. Lett.,* 1999, 1, 1129-1132.

(69) F. Li, S. Gentemann, W. A. Kalsbeck, J. Seth, J. S. Lindsey, D. Holten and D. F. Bocian, *J. Mater. Chem.,* 1997, 7, 1245-1262.

(70) H. L. Kee, C. Kirmaier, L. Yu, P. Thamyongkit, W. J. Youngblood, M. E. Calder, L. Ramos, B. C. Noll, D. F. Bocian, W. R. Scheidt, R. R. Birge, J. S. Lindsey and D. Holten, *J. Phys. Chem. B,* 2005, 109, 20433-20443.

(71) A. T. Gradyushko, A. N. Sevchenko, K. N. Solovyov and M. P. Tsvirko, *Photochem. Photobiol.,* 1970, 11, 387-400.

(72) G. Weber and F. W. J. Teale, *Trans, Faraday Soc.,* 1957, 53, 646-655.

(73) Except for molecular mechanics and semi-empirical models, the calculation methods used in Spartan have been documented in Y. Shao, L. F. Molnar, Y. Jung, J. Kussmann, C. Ochsenfeld, S. T. Brown, A. T. B. Gilbert, L. V. Slipchenko, S. V. Levchenko, D. P. O'Neill, R. A. DiStasio Jr., R. C. Lochan, T. Wang, G. J. O. Beran, N. A. Besley, J. M. Herbert, C. Y. Lin, T. Van Voorhis, S. H. Chien, A. Sodt, R. P. Steele, V. A. Rassolov, P. E. Maslen, P. P. Korambath, R. D. Adamson, B. Austin, J. Baker, E. F. C. Byrd, H. Dachsel, R. J. Doerksen, A. Dreuw, B. D. Dunietz, A. D. Dutoi, T. R. Furlani, S. R. Gwaltney, A. Heyden, S. Hirata, C.-P. Hsu, G. Kedziora, R. Z. Khalliulin, P. Klunzinger, A. M. Lee, M. S. Lee, W.-Z. Liang, I. Lotan, N. Nair, B. Peters, E. I. Proynov, P. A. Pieniazek, Y. M. Rhee, J. Ritchie, E. Rosta, C. D. Sherrill, A. C. Simmonett, J. E. Subotnik, H. L. Woodcock III, W. Zhang, A. T. Bell, A. K. Chakraborty, D. M. Chipman, F. J. Keil, A. Warshel, W. J. Hehre, H. F. Schaefer III, J. Kong, A. I. Krylov, P. M. W. Gill and M. Head-Gordon, *Phys. Chem. Chem. Phys.,* 2006, 8, 3172-3191.

The foregoing is illustrative of the present invention, and is not to be construed as limiting thereof. The invention is defined by the following claims, with equivalents of the claims to be included therein.

That which is claimed:

1. A compound of Formula I:

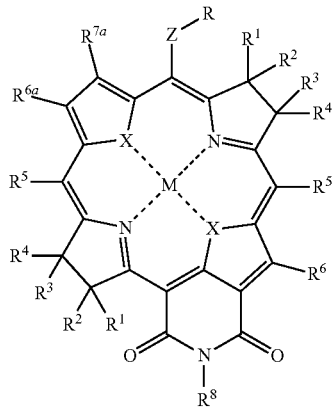

wherein:
M is a metal or is absent;
each X is independently selected from the group consisting of Se, NH, $CH_2$, O and S;
Z is O, S or a covalent bond;
R and each $R^1$ and $R^2$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; or $R^1$ and $R^2$ together are =O or spiroalkyl;
each $R^3$ and $R^4$ is independently selected from the group consisting of alkyl, cycloalkyl, aryl, and arylalkyl;
each $R^5$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; and
$R^6$, $R^{6a}$ and $R^{7a}$ are each independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups; and
$R^8$ is selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, targeting groups, and surface attachment groups;
or a pharmaceutically acceptable salt thereof.

2. The compound of claim 1, wherein M is present and is selected from the group consisting of Pd, Pt, Mg, Zn, Al, Ga, In, Sn, Cu, Ni, and Au.

3. The compound of claim 1, wherein each X is NH.

4. The compound of claim 1, wherein Z is O.

5. The compound of claim 1, wherein Z is S.

6. The compound of claim 1, wherein Z is a covalent bond.

7. A compound of claim 1 wherein said targeting group is selected from the group consisting of proteins, peptides, and nucleic acids.

8. A composition consisting of a compound of claim 1, in a solvent, wherein: said composition has a peak molar absorption coefficient in solution of 10,000 to 300,000 $M^{-1}cm^{-1}$ at a wavelength between 700 and 1000 nanometers; and/or said composition has a loss of not more than 20 percent of said compound when stored in a sealed vessel at room temperature in the absence of ambient light for at least 3 months.

9. A pharmaceutical composition comprising a compound of claim 1 in a pharmaceutically acceptable carrier.

10. The compound of claim 1, wherein:
each X is NH; and
Z is O.

11. The compound of claim 10, wherein said targeting group is selected from the group consisting of proteins, peptides, and nucleic acids.

12. The compound of claim 11, wherein said compound has the structure:

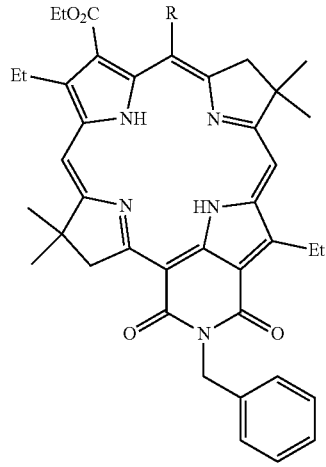

where R is OMe.

13. The compound of claim 1, wherein:
each X is NH;
M is absent;
Z is O;
R is H;
each $R^1$ and $R^2$ is independently selected alkyl;
each $R^3$ and $R^4$ is independently selected alkyl;
each $R^5$ is H;
$R^6$, $R^{6a}$ are each independently selected from alkyl;
$R^{7a}$ is ester; and
$R^8$ is arylalkyl;
or a pharmaceutically acceptable salt thereof.

14. The compound of claim 1, wherein:
each X is NH;
M is a metal or is absent, and when present is selected from the group consisting of Pd, Pt, Mg, Zn, Al, Ga, In, Sn, Cu, Ni, and Au;
Z is O, S or a covalent bond;
R is H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, hydrophilic groups, and targeting groups;
each $R^1$ and $R^2$ is independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, hydrophilic groups, and targeting groups; or $R^1$ and $R^2$ together are =O or spiroalkyl;
each $R^3$ and $R^4$ is independently selected from the group consisting of alkyl, cycloalkyl, aryl, and arylalkyl;
each $R^5$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, hydrophilic groups, and targeting groups; and
$R^6$ and $R^{6a}$ are each independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, hydrophilic groups, and targeting groups; and
$R^{7a}$ is selected from the group consisting of ester, amide, alkoxylacylamino, aminoacyloxy, hydrophilic groups, and targeting groups; and
$R^8$ is selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, hydrophilic groups, and targeting groups;
wherein each said targeting group is selected from the group consisting of proteins, peptides, and nucleic acids;
or a pharmaceutically acceptable salt thereof.

15. The compound of claim 1, wherein:
each X is NH;
M is a metal or is absent, and when present is selected from the group consisting of Pd, Pt, Mg, Zn, Al, Ga, In, Sn, Cu, Ni, and Au;
Z is O, S or a covalent bond;
R is H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, hydrophilic groups, and targeting groups;
each $R^1$ and $R^2$ is independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, hydrophilic groups, and targeting groups; or $R^1$ and $R^2$ together are =O or spiroalkyl;
each $R^3$ and $R^4$ is independently selected from the group consisting of alkyl, cycloalkyl, aryl, and arylalkyl;
each $R^5$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, hydrophilic groups and targeting groups; and
$R^6$ and $R^{6a}$ are each independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, hydrophilic groups, and targeting groups; and
$R^{7a}$ is selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, hydrophilic groups, and targeting groups; and
$R^8$ is selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, hydrophilic groups, and targeting groups;
wherein each said targeting group is selected from the group consisting of proteins, peptides, and nucleic acids;
or a pharmaceutically acceptable salt thereof.

16. The compound of claim 1, wherein:

each X is NH;

M is a metal or is absent, and when present is selected from the group consisting of Pd, Pt, Mg, Zn, Al, Ga, In, Sn, Cu, Ni, and Au;

Z is O, S or a covalent bond;

R is H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, and targeting groups, each $R^1$ and $R^2$ is independently selected from the group consisting alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, and targeting groups; or $R^1$ and $R^2$ together are =O or spiroalkyl;

each $R^3$ and $R^4$ is independently selected from the group consisting of alkyl, cycloalkyl, aryl, and arylalkyl;

each $R^5$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, and targeting groups; and $R^6$ and $R^{6a}$ are each independently selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, and targeting groups; and $R^{7a}$ is selected from the group consisting of alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, and targeting groups; and $R^8$ is selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, phosphate, phosphonate, urea, alkoxylacylamino, aminoacyloxy, linking groups, hydrophilic groups, and targeting groups;

wherein each said targeting group is selected from the group consisting of proteins, peptides, and nucleic acids;

or a pharmaceutically acceptable salt thereof.

* * * * *